United States Patent
Tokhtuev et al.

(10) Patent No.: US 8,076,155 B2
(45) Date of Patent: Dec. 13, 2011

(54) WIDE RANGE KINETIC DETERMINATION OF PERACID AND/OR PEROXIDE CONCENTRATIONS

(75) Inventors: Eugene Tokhtuev, Duluth, MN (US);
Christopher Owen, Duluth, MN (US);
Paul R. Kraus, Apple Valley, MN (US);
Joseph Erickson, Cloquet, MN (US);
Paul Schilling, Duluth, MN (US);
Daniel Kamben, Duluth, MN (US);
William Christensen, Hibbing, MN (US); Viktor Slobodyan, Duluth, MN (US)

(73) Assignee: Ecolab USA Inc., Saint Paul, MN (US)

( * ) Notice: Subject to any disclaimer, the term of this patent is extended or adjusted under 35 U.S.C. 154(b) by 29 days.

(21) Appl. No.: 12/370,369

(22) Filed: Feb. 12, 2009

(65) Prior Publication Data
US 2009/0150086 A1      Jun. 11, 2009

Related U.S. Application Data

(63) Continuation-in-part of application No. 11/810,417, filed on Jun. 5, 2007.

(51) Int. Cl.
*G01N 21/00* (2006.01)

(52) U.S. Cl. ........ 436/164; 436/139; 436/135; 436/165; 436/166; 436/171; 422/68.1; 422/82.05; 422/82.09; 374/142; 374/E13.001; 356/246

(58) Field of Classification Search ............... 422/82.09, 422/68.1, 82.05; 436/129, 135, 166, 171, 436/164, 165; 374/142, E13.001; 356/246
See application file for complete search history.

(56) References Cited

U.S. PATENT DOCUMENTS
2007/0064228 A1    3/2007  Tartakovsky et al.

FOREIGN PATENT DOCUMENTS
WO    2006043855    4/2006

OTHER PUBLICATIONS

Pettas et al, "Simultaneous spectra-kinetic determination of peracetic acid and hydrogen peroxide in a brewery cleaning-in-place disinfection process", Analytical Chimica Acta, 522, 2004, pp. 275-280.*
Harms et al, "Rapid and selective determination of peroxyacetic acid in disinfectants using flow injection analysis", Analytica Chimica Acta, 389, 1999, pp. 233-238.*
Davies et al, "Determination of Peracids in the Presence of a large excess of hydrogn peroxide using a rapid and convenient spectrophotometric method", Analyst, 1988, 113, 1477-1479.*
English-language abstract for WO2006043855 (Grinevich et al.).

* cited by examiner

*Primary Examiner* — In Suk Bullock
*Assistant Examiner* — Dennis M White
(74) *Attorney, Agent, or Firm* — Fredrikson & Byron, P.A.

(57) ABSTRACT

A use composition monitor determines the concentration of peracid and/or peroxide in a use composition using a kinetic assay procedure. A sample mixture containing a sample of the use composition, a diluent and at least one reagent is prepared and analyzed using, for example, an optical detector. Response data obtained by the detector is indicative of the optical absorbance of the sample mixture as a function of time. A processor analyzes the response data to determine a corresponding best fit linear relationship. Depending upon an expected concentration range, the initial absorbance and/or the slope of the best fit equation are used to calculate the concentrations of the peracid and peroxide in the use composition.

33 Claims, 20 Drawing Sheets

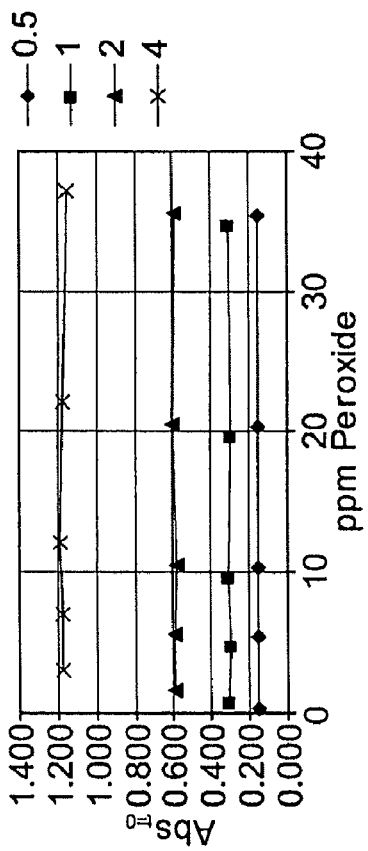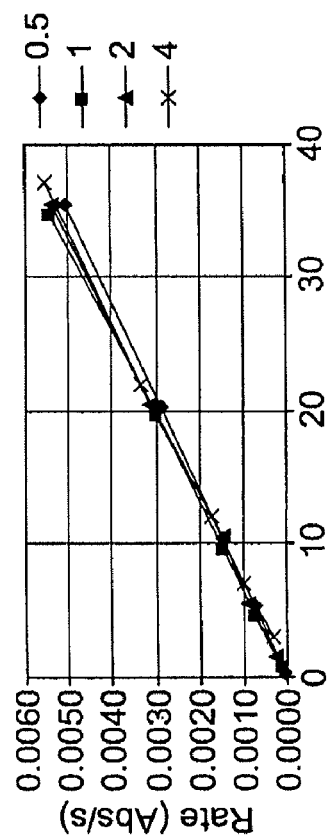
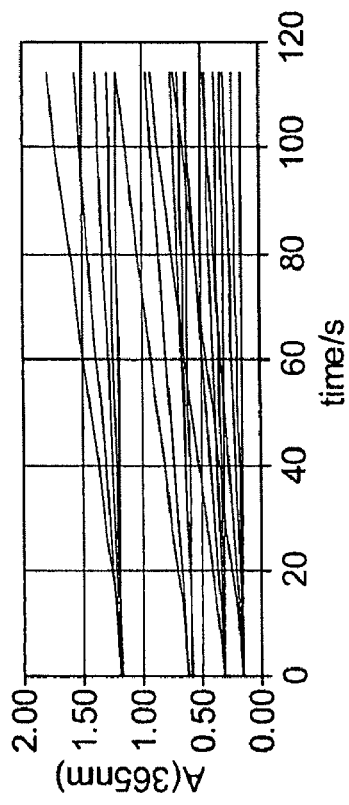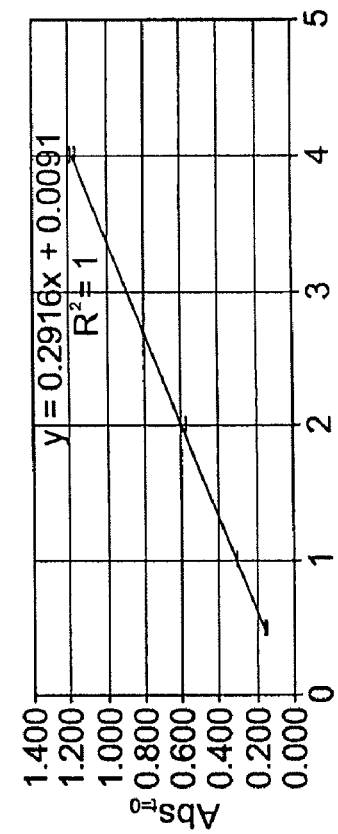
Fig. 3A
Fig. 3B
Fig. 3C
Fig. 3D

WIDE RANGE KINETIC DETERMINATION OF PERACID AND/OR PEROXIDE CONCENTRATIONS

CROSS-REFERENCE TO RELATED APPLICATIONS

This application is a continuation-in-part of U.S. patent application Ser. No. 11/810,417, filed on Jun. 5, 2007 and titled "KINETIC DETERMINATION OF PERACID AND/OR PEROXIDE CONCENTRATIONS."

CROSS-REFERENCE TO RELATED APPLICATIONS

The present application is related to the following commonly assigned utility patent applications, all of which are hereby incorporated by reference in their entireties: A) U.S. patent application Ser. No. 12/370,331, filed on Feb. 12, 2009, titled "OPTICAL CELL" B) U.S. patent application Ser. No. 12/370,348, filed Feb. 12, 2009, titled "TEMPERATURE STABILIZED OPTICAL CELL", and C) U.S. patent application Ser. No. 12/370,358, filed on Feb. 12, 2009, titled "METHOD OF CALIBRATION FOR NONLINEAR OPTICAL SENSOR".

FIELD OF THE INVENTION

The present invention relates to apparatus and methods for determining the concentrations of peracid and hydrogen peroxide in a use composition.

BACKGROUND

Antimicrobial compositions are used in a variety of automated processing and cleaning applications to reduce microbial or viral populations on hard or soft surfaces or in a body or stream of water. For example, antimicrobial compositions are used in various applications including kitchens, bathrooms, factories, hospitals and dental offices. Antimicrobial compositions are also useful in the cleaning or sanitizing of containers, processing facilities or equipment in the food service or food processing industries, such as cold or hot aseptic packaging. Antimicrobial compositions are also used in many other applications including but not limited to clean-in-place systems (CIP), clean-out-of-place systems (COP), washer-decontaminators, sterilizers, textile laundry machines, filtration systems, etc.

Whatever the application, an antimicrobial or "use" composition is a composition containing a defined minimum concentration of one or more active components which exhibit desired antimicrobial properties. One such category of active antimicrobial component are peracids, such as peroxycarboxylic acid (peracid), peroxyacid, peroxyacetic acid, peracetic acid, peroctanoic acid, peroxyoctanoic acid and others. The concentration of active components in the use composition is chosen to achieve the requisite level of antimicrobial activity. In use compositions in which one or more peracids are the active component, and in the instance of a recirculating process, the concentration of hydrogen peroxide tends to increase over time while the concentration of peracid decreases. However, in order to maintain the requisite level of antimicrobial activity, the amount of peracid in the use composition must be maintained at a defined minimum concentration. In addition, as the amount of hydrogen peroxide in the use composition increases, the use composition may exceed a defined maximum concentration of hydrogen peroxide in the solution. In some applications, for example bottling line cleansing, the allowable amount of residual hydrogen peroxide is subject to government regulations. Once the hydrogen peroxide concentration exceeds the maximum concentration, the spent use composition is discarded and a new use composition generated.

To ensure that the amount of peracid is maintained at or above some minimum concentration and to determine when the amount of hydrogen peroxide reaches or exceeds a maximum concentration, it is necessary to determine the concentration of peracid(s) and hydrogen peroxide in the use composition. In the past, to determine both the peracid concentration and the hydrogen peroxide concentration in a use composition has required multiple time consuming manual titrations, several different reagents and relatively large volumes of use composition. Moreover, past devices and methods for determining both peracid and hydrogen peroxide concentrations were effective over only a narrow range of concentrations.

SUMMARY

In general, the disclosure relates to apparatus and methods for determining the concentration of peracid and/or hydrogen peroxide in a use composition. The apparatus and/or methods measure the concentration of peracid and/or the concentration of hydrogen peroxide in a sample of the use composition using a kinetic assay procedure.

In one aspect, the invention is directed to a method for determining a concentration of peracid and/or peroxide within a use composition. The method includes selecting an expected concentration range within which the concentrations of the peracid and/or peroxide are expected to fall. In some embodiments, the expected range depends upon an application employing the use composition. A sample which includes the use composition, a diluent, and one or more reagents is prepared within a sample line. In some embodiments, the sample further includes an acid. In some embodiments, the step of preparing the sample can depend upon the expected concentration range. The sample can be mixed within the sample line and delivered to an optical cell. An optical response of the sample mixture is measured to obtain response data indicative of absorbance of the sample as a function of time. The concentrations of the peracid and peroxide within the use composition are determined based upon the response data. In some embodiments, the method used to determine the concentrations of peracid and peroxide depends upon the expected concentration value. Moreover, in some embodiments of the method, a calibration step is included prior to execution of some or all of the steps. In addition, in some embodiments, the steps of mixing the sample, delivering the sample, and measuring the optical response can be performed within a temperature-regulated local environment.

In another aspect a system for determining the concentrations of peracid and peroxide within a use composition over a wide concentration range is disclosed. Such a system includes an optical detector for obtaining response data from a sample which comprises the use composition, a diluent, and at least one reagent. The response data is indicative of the concentrations of the peracid and peroxide within the use composition. A processor connected with the optical sensor is configured to determine the concentration of the peracid and/or the peroxide based upon the response data. An expected concentration range selected and stored within the processor determines which method the processor will use to determine the concentrations of the peracid and/or peroxide. In some embodiments, the optical detector can be a reduced-turbulence detector. In addition, some embodiments include a laminar flow mixer for mixing the sample prior to measurement by the optical detector. Moreover, in some embodiments, the optical detector and laminar flow mixer can be temperature regulated.

In some embodiments, methods and devices according to the invention provide for the determination of peracid and peroxide concentrations within a use composition. In particular, embodiments can provide such determination across a wide range of concentrations. Thus, embodiments can allow for the use of a single device or method in a variety of applications and locations. Moreover, some embodiments can be adapted for use under a wide range of operating conditions. In addition, some embodiments can provide improved precision within the expected concentration range.

The details of one or more embodiments of the invention are set forth in the accompanying drawings and the description below. Other features of the invention will be apparent from the description and drawings, and from the claims.

BRIEF DESCRIPTION OF THE DRAWINGS

The following drawings are illustrative of particular embodiments of the invention and therefore do not limit the scope of the invention. The drawings are not to scale (unless so stated) and are intended for use in conjunction with the explanations in the following detailed description. Embodiments of the invention will hereinafter be described in conjunction with the appended drawings, wherein like numerals denote like elements.

FIGS. 3A-3D show plots of absorbance versus time, absorbance versus peroxide concentration, absorbance versus peracid concentration and rate of absorbance versus peroxide concentration, respectively, for a sample iodide solution.

DETAILED DESCRIPTION

The present invention relates to apparatus and/or methods for determining the concentrations of peracid and/or hydrogen peroxide in a use composition. The apparatus and/or methods measure the concentration of peracid and/or the concentration of hydrogen peroxide (hereinafter referred to simply as "peroxide" or $H_2O_2$) in a sample of the use composition using a kinetic assay procedure.

Figure 1:
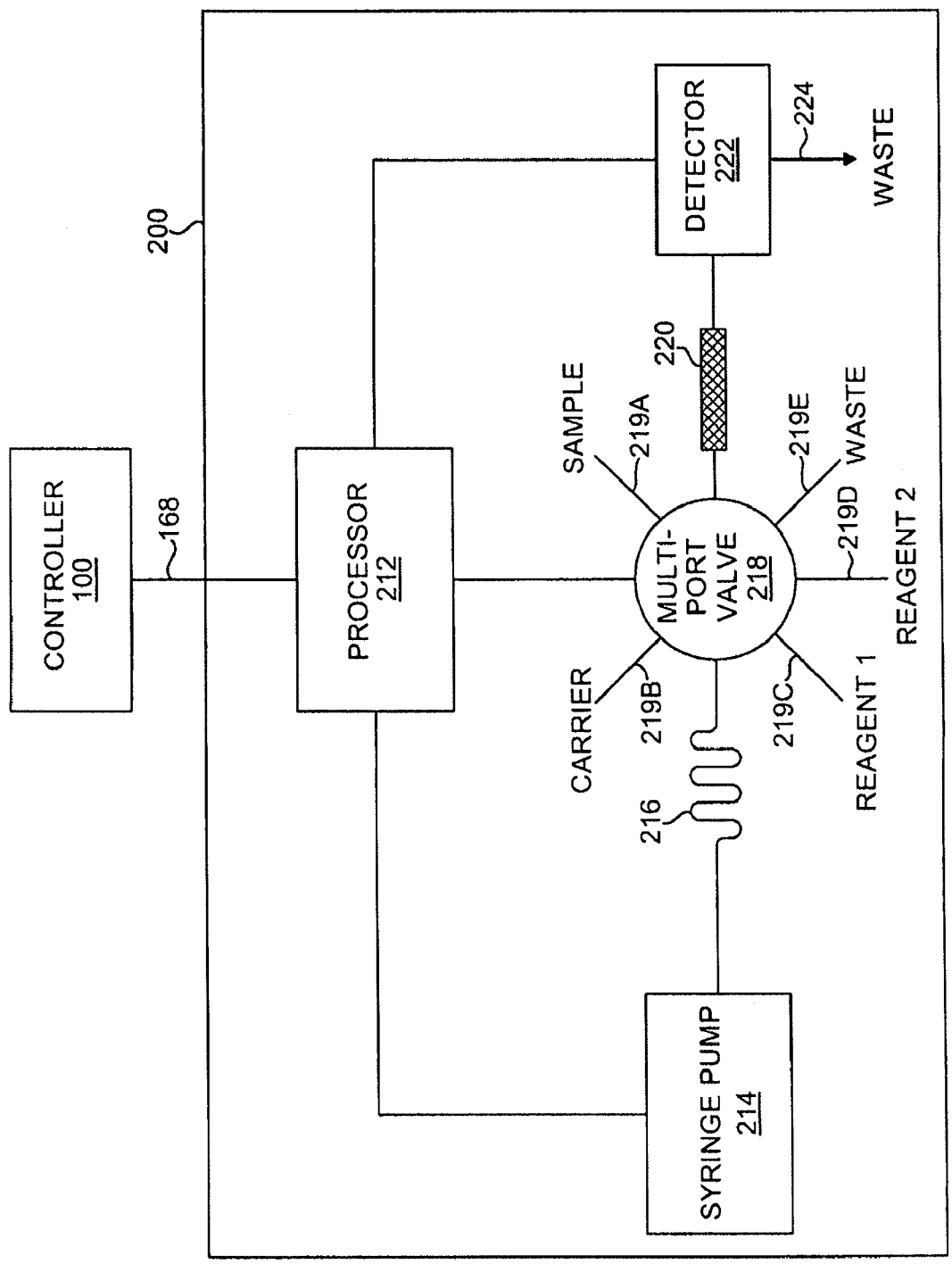
FIG. 1 shows a schematic diagram illustrating an example embodiment of use composition monitor 200.

FIG. 1 shows a schematic diagram illustrating an example embodiment of a use composition monitor 200 and an optional controller 100. Use composition monitor 200 may monitor the use composition to determine the content of any selected analyte. As discussed herein, use composition monitor 200 determines the concentration of peracid and/or hydrogen peroxide in the use composition. For example, the use composition may be monitored to ensure that the concentration of peracid satisfies at least a minimum threshold concentration. The use composition may also be monitored to determine when the concentration of hydrogen peroxide exceeds a maximum threshold concentration.

As used herein, the term "peracid" refers to any acid that in which the hydroxyl group (—OH) is replaced with the peroxy group (—OOH). The peracid(s) may be C2-C18 peracid(s), such as C2 (peracetic) acid and C8 (peroctanoic) acid. It shall be understood that the apparatus and/or methods of the present invention may detect the combined presence of all peracids in a sample, whether the sample contains one or more than one different peracids, and that the invention is not limited in this respect.

Peroxycarboxylic acids generally have the formula $R(CO_3H)_n$. In some embodiments, the R may be an alkyl, arylalkyl, cycloalkyl, aromatic or heterocyclic group, and n may be one or two.

Peroxycarboxylic acids useful in this invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysubric acid and mixtures thereof as well others known to those of skill in the art.

The concentrations of peracid and/or peroxide determined by use composition monitor 200 may be used, for example, as feedback to controller 100 to maintain the peracid concentration in the use composition within a predefined range and/or to cause the emptying of the use composition vessel and production of a new use composition when the hydrogen peroxide concentration exceeds the maximum peroxide threshold concentration. If, for example, the concentration of peracid in the use composition decreases below a predetermined level, the use composition may be replenished by adding a concentrated peracid composition to the use composition. As another example, if the concentration of peroxide in the use composition exceeds a predetermined level, the use composition may be replenished by emptying the use composition vessel of the spent use composition and generating a new use composition.

In the embodiment shown in FIG. 1, use composition monitor 200 includes a sequential injection analysis (SIA) manifold under control of a processor 212. The SIA manifold includes a syringe pump 214, a holding coil 216, a multi-position (multi-port) valve 218, a static mixer 220 and a detector 222. The SIA manifold is a device that enables automation of manual wet chemical analytical procedures. In other embodiments, other optical-based or electromechanical detectors could also be used, and the invention is not limited in this respect.

Multi-port valve 218 may be implemented using a computer controlled valve that allows selection of one or more ports to intake (aspirate) or expel (dispense) samples, reagents or carriers as necessary in a particular application. Multi-port valve 218 is connected to receive a sample of the use composition, at least one carrier and at least one reagent along lines 219A, 219B, 219C and 219D respectively. Multi-port valve is also connected to a waste line 219E.

The resultant streams including the samples, reagents and carriers move through the system and into the detector 222 via appropriate tubing. The tubing may be narrow bore tubing with, for example, an inside diameter (ID) of 0.5 mm to 2 mm. Suitable multi-port valves include Cheminert valve Model C25-3184, C25-3186, C25-3188 or C25-3180 multi-port valves with 4, 6, 8 and 10 positions, respectively, available from VICI Valco Instruments Co. Inc., Houston, Tex. Another example of a suitable valve is the M-470 6-Way Medium Pressure Selection Valve available from Upchurch Scientific, Oak Harbor, Wash.

In the embodiment shown in FIG. 1, software running on processor 212 controls the system protocol resulting in aspiration of the sample, reagent(s) and carrier and their transport to detector 222 for analysis. Software running on processor 212 also analyzes response data received from detector 222 and determines the concentrations of peracid and peroxide in the use composition based on the response data.

Syringe pump 214 is preferably a computer controllable bi-directional pump capable of measuring small volumes (as low as 5-10 µl, for example) with high precision. The syringe pump does not become contaminated as the solutions are only drawn into holding coil 216 and not into the syringe. An example suitable syringe pump is the MicroCSP-3000 available from FIAlab Instruments, Bellevue, Wash. An example of other suitable pumps are the M6 or M50 syringe-free pumps available from VICI Valco Instruments Co. Inc., Houston, Tex. However, it shall be understood that any suitable pump may be used without departing from the scope of the present invention, and that the invention is not limited in this respect.

Holding coil 216 at various time throughout the measurement sequence temporarily holds the sample, carrier and/or reagent(s) after they are drawn in by syringe pump 214. A suitable holding coil may be cut from a suitable length of tubing; for example a 1 ml holding coil may be made using 220 cm of 0.030" ID tubing. However, it shall be understood that any suitable holding coil may be used without departing from the scope of the present invention, and that the invention is not limited in this respect.

When syringe pump flow is reversed, the fluid volume temporarily stored in holding coil 216 flows from the holding coil 216 through the multi-port valve 218 and into the static mixer 220. Static mixer provides thorough mixing of the sample, reagent and carrier to ensure that the response data measured by the detector 222 leads to an accurate determination of the concentrations of peracid and peroxide in the use composition. The static mixer 220 may be implemented using any conventional device designed to rapidly mix together two or more fluids. For example, static mixer 220 may be a piece of tubing with internal baffles that cause flow reversal of the fluids to result in rapid mixing. Static mixer 220 may also be implemented using a knotted reactor, reaction coil, serpentine or other fluid mixing device known in the art. An example baffle-type static mixer is the Series 120 Individual Mixing Elements available from TAH Industries Inc, Robbinsville, N.J. However, it shall be understood that any suitable mixer may be used without departing from the scope of the present invention, and that the invention is not limited in this respect.

In some embodiments, the static mixer can be replaced with a laminar flow mixer. Laminar flow mixing is accomplished by allowing adjacent components of the sample to bleed into one another as the sample is driven through the sample line. Such a mixer can provide for non-turbulent mixing of the sample. An appropriate laminar flow mixer can comprise a length of tubing. In some embodiments, the tubing is coiled to preserve space and allow for stowing within the device. In some embodiments, a laminar mixing coil comprising approximately 80 inches of tubing is used to mix the sample within the sample line prior to reaching detector 222.

Detector 222 measures at least one characteristic of the sample mixture indicative of the concentrations of peracid and/or hydrogen peroxide in the use composition. The measurements obtained by detector 222 are referred to herein as "response data." Processor 212 determines the concentration of peracid and/or peroxide in the use composition based on the response data. In one embodiment, detector 222 is an optical detector that measures the transmittance and/or the absorbance of the sample. In that embodiment, the response data may be the optical transmittance data or optical absorbance data of the sample as a function of time. In other embodiments, detector 222 may measure other characteristics indicative of the concentrations of peracid and/or peroxide in the sample, such as fluorescence, pH, oxidation-reduction potential, conductivity, mass spectra and/or combinations thereof. In those embodiments, the response data would be the corresponding measured characteristic at the appropriate points in time. Example detectors 222 include photometric detectors operating in the visible, ultraviolet or infrared wavelength range, although other luminescence detection techniques may also be used without departing from the scope of the present invention. One example of a suitable commercially available photometric detector can be assembled using a DH-2000 Deuterium Tungsten Halogen Light Source, FIA-Z-SMA Flow Cell and USB4000 Miniature Fiber Optic Spectrometer, all available from Ocean Optics Inc., Dunedin, Fla. Example embodiments of suitable optical detectors are also described herein with respect to FIGS. 6-10. It shall be understood, however, that any suitable optical detector may be used without departing from the scope of the present invention, and that the invention is not limited in this respect.

In the case of an optical detector, the voltage response of the detector corresponds to the amount of the light transmitted through the sample mixture. Detector 222 thus essentially measures the change of the sample solution optical properties within detector 222 as a function of time. The transmittance is the ratio of the intensity of light coming out of the sample (I) to intensity of light incident to the sample ($I_0$), $T=I/I_0$. Once the transmittance of the sample is measured, the absorbance (A) of the sample may be calculated. The absorbance or optical density (A) is a logarithmic function of the transmittance; $A=-\log_{10} T=-\log_{10} I/I_0=\log_{10} I_0/I$. As is discussed in further detail below, the initial absorbance of the sample ($A_0$) is indicative of the concentration of peracid in the use composition and the sample absorbance variation over time is indicative of the concentration of hydrogen peroxide in the use composition. However, as is further indicated, this relationship may not hold true across wide ranging use composition concentrations. For example, at higher concentrations, e.g. above 500 ppm peracid, concentration of peracid is a function of both initial absorbance and, to a lesser degree, absorbance over time. Accordingly, to provide instruments capable of accommodating use with a wide concentration range, i.e. a range encompassing both concentration ranges described above, alternative methods must be utilized.

The reagent(s) and carriers may be selected to provide an analytical test that reproducibly generates accurate response data. In one embodiment, the reagent may include a buffered iodide solution. In other embodiments, such as a multiple reagent system, the reagents may include an iodide solution, such as potassium iodide, with the pH adjusted to the alkaline range and a dilute acid such as acetic acid to adjust the pH of the reacting species to a pH less than approximately 6.5. The carrier may include water, deionized water or other appropriate carrier. However, it shall be understood that other suitable reagents and carriers may also be used without departing from the scope of the present invention, and that the invention is not limited in this respect.

The molar concentration of the reagent(s) may depend upon the range of expected concentrations of peracid and peroxide in the use composition. For example, for a peracetic concentration in the use composition in the range of about 1500 to about 2000 ppm, the molar concentration of the peracid may be in the range of about 0.0197 to about 0.0263.

Figure 2:
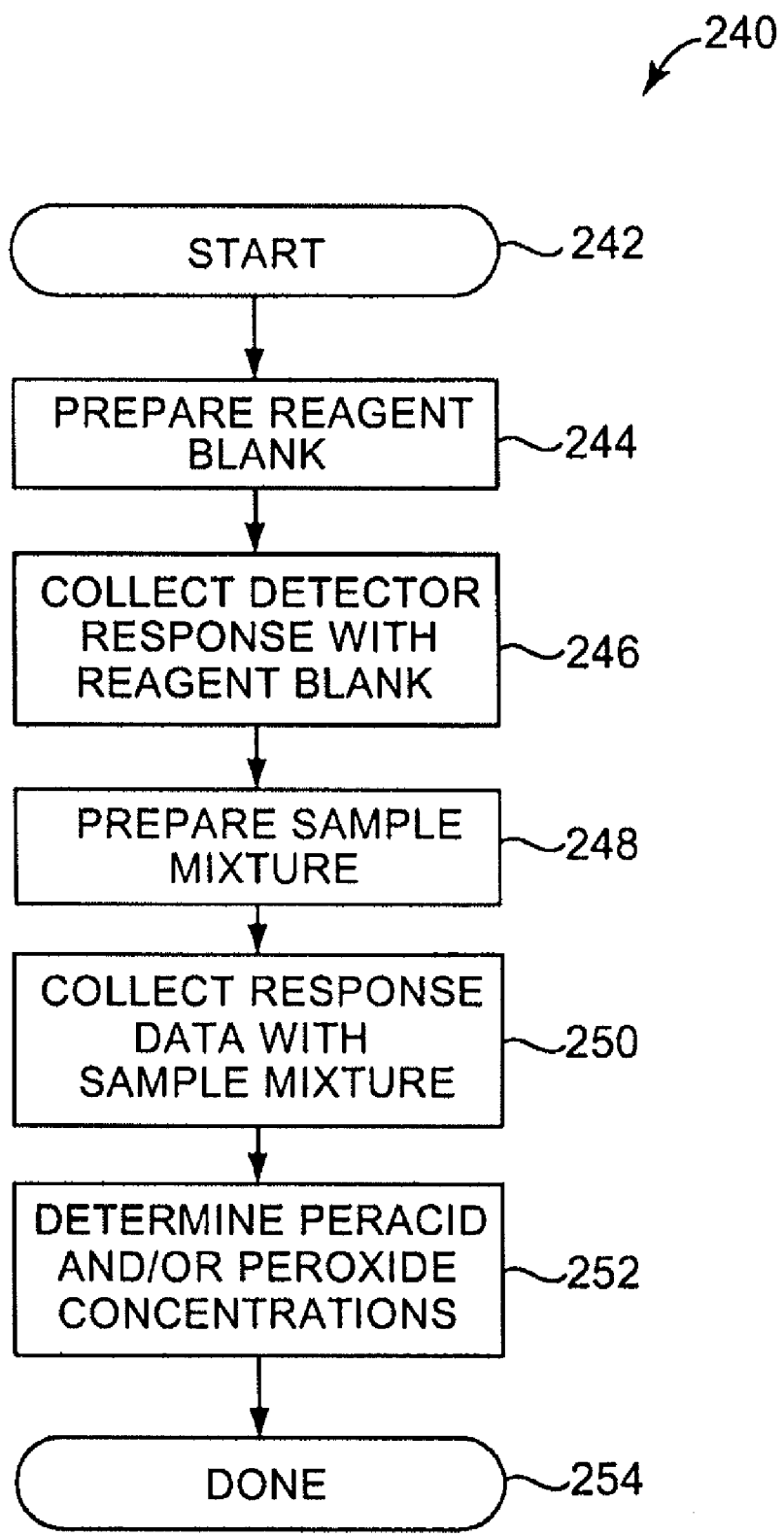
FIG. 2 is a flow chart illustrating a sequence (240) carried out by use composition monitor 200 to collect response data and determine the concentration of peroxyacetic acid and/or hydrogen peroxide in a use composition.

FIG. 2 is a flow chart illustrating a measurement sequence (240) carried out by use composition monitor 200 to collect response data and determine the concentration of peroxyacetic acid and/or hydrogen peroxide in a use composition. In one embodiment, use composition monitor 200 may be programmed to determine the concentrations of peracid and hydrogen peroxide on a periodic basis. The frequency at which monitoring device 200 determines the concentration of peracid and hydrogen peroxide in the use composition is referred to herein as the "monitoring frequency." For example, monitoring device 200 may be programmed to monitor the concentrations of peracid and hydrogen peroxide in the use composition every 15 minutes, every 30 minutes, every hour, every two hours, every day or other appropriate time. The monitoring frequency/interval may vary depending on, among other things, the particular application to which the use composition is directed and the corresponding threshold concentrations of peracid and hydrogen peroxide.

At the start (242) of each measurement sequence, processor 212 manages preparation of a reagent blank (244) and collects the voltage response of the detector with the reagent blank (246). The reagent blank is a volume containing only the carrier and the reagent(s), i.e., the reagent blank does not include any use composition. The reagent blank allows the system to compensate for any variations in the reagent or the carrier, such as variations in color or other variations, which might affect the transmittance of the sample mixture and thus the resulting voltage response of the detector. The voltage response of the detector measured using the reagent blank may then be used as a reference voltage during calculation of the absorbance of the sample mixture.

Processor 212 manages a sequence of drawing in of the carrier, reagent, dilute acid (if used), and use composition sample and dispensing them through the static mixer and into the detector to prepare the sample mixture (248). Once detector 222 receives the sample mixture, processor 212 collects the response data from detector 222 (250). In the case of an optical detector, the response data is the measured change in the optical response of the detector over time. In one embodiment, detector 222 measures response data by measuring the color change (e.g., absorbance or transmittance) of the sample solution within detector 222 as a function of time. In other words, the voltage response of detector 222 as a function of time corresponds to the amount of light transmitted through the sample mixture and hence the color the of the sample mixture as the chemical reaction progresses. The response data is indicative of the concentrations of peracid and hydrogen peroxide in the use composition.

The time frame during which processor 212 collects response data from detector 222 is referred to herein as the "measurement interval." The frequency at which processor 212 collects the measurements of detector 222 is referred to herein as the "measurement rate." The response data is the plurality of measurements captured by processor 212 from detector 222 during the measurement interval. The measurement interval may be anywhere between, for example, about 10 seconds and about 4 minutes. The measurement rate may be anywhere between 1 and 100 or more measurements per second. In one example embodiment, the measurement interval is about 2 minutes and the measurement rate is 2 measurements per second. The measurements interval and the measurement rate may vary depending upon, among other things, the particular application to which the use composition is directed and the corresponding threshold concentrations of peracid and hydrogen peroxide in the use composition. The measurement rate may also be influenced by the resolution of the electronics.

Once processor 212 collects the response data, processor 212 determines the concentrations of peracid and/or hydrogen peroxide in the use composition based on the response data (252). This process is described in more detail herein with respect to FIGS. 3A-3D and FIG. 4. The measurement sequence is then complete (254). Processor 212 may then wait for the next monitoring interval or for a user request and repeat the sequence 240 with a new sample of use composition.

Figure 10:
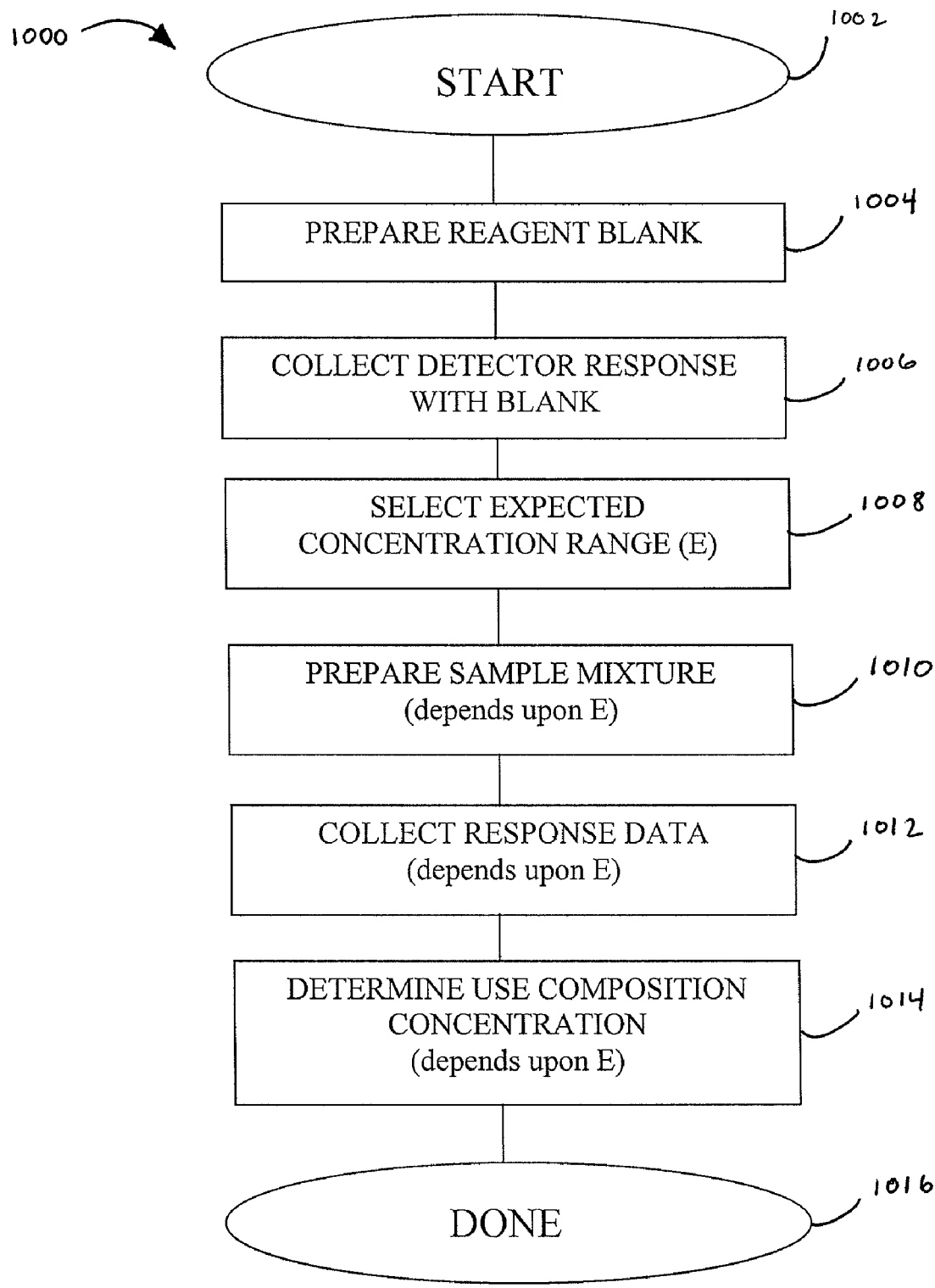
FIG. 10 is a flow chart illustrating a procedure by which a processor can determine the concentrations of peracid and hydrogen peroxide from response data according to some embodiments.

FIG. 10 is a flow chart illustrating an alternative measurement sequence 1000 to the above described measurement sequence. Alternative measurement sequence 1000 can be carried out by use composition monitor 200 or variations on use composition monitor 200 described herein to collect response data and determine the concentration of peracid and/or hydrogen peroxide in a use composition. In some embodiments, use composition monitor may be programmed to determine the concentrations of peracid and hydrogen peroxide on a periodic basis based on a monitoring frequency as described above. The monitoring frequency/interval may vary depending on, among other things, the particular application to which the use composition is directed and the corresponding threshold concentrations of peracid and hydrogen peroxide.

At the start (1002) of each alternative measurement sequence 1000, the processor 212 manages preparation of a reagent blank (1004) and collects the voltage response of the detector with the reagent blank (1006). These two steps are generally analogous with the above described first two steps (244, 246) of the measurement sequence 240 of FIG. 2. In some embodiments, the measurement of an actual reagent blank need not be performed during every measurement sequence, but can be performed periodically, e.g. once per week or month. For such variants, the absorbance (optical density) of rinsing water during each measurement cycle can be used as a reagent blank (zero absorbance level).

According to the alternative measurement sequence 1000, an expected concentration range E for one or more of the analytes is selected (1008). The selection of an expected concentration range E can occur prior to the start of the measurement sequence or at an early stage prior to the use composition sample preparation and analysis steps, e.g. after the preparation of the reagent blank (1004) and collection of response data of the reagent blank (1006). In some embodiments, the selection of the expected concentration range is a static operation wherein a range selected during one measurement sequence or another operation (e.g. the expected range can be pre-programmed) is utilized for subsequent measurement sequences.

The expected concentration range selection can be conveyed to the controller by user input or memory indicating a specified range, or the selection of a pre-determined range. Pre-determined range selections can comprise application independent concentration ranges (e.g. selection between "high" and "low" concentration ranges) or concentration ranges keyed to particular uses, applications, or environments with which the measurement is associated. For example, application specific concentrations can comprise: Aseptic bottle rinse comprising 1000-5000 ppm peroxyacetic acid and 5000-40,000 ppm hydrogen peroxide, or Central Sanitizer comprising 100-1000 ppm peracid and 100-5000 ppm hydrogen peroxide. Moreover, in some embodiments, the step of selecting the expected concentration range can comprise an adaptive selection process. In an adaptive selection process, the expected concentration range is selected by measuring the optical response of an initial sample and determining whether the response data of the initial sample is appropriate. The controller can then iteratively change the volume of components of the sample (preferably, the diluent, use composition, or both diluent and use composition), measuring the optical response of the sample until appropriate response data is collected. In any case, the selected expected concentration range is then used in subsequent steps to determine the appropriate parameters for calculating accurate concentration values.

Subsequent to the selection of an expected concentration range (1008), processor 212 manages a sequence of drawing in the constituent parts of the sample and dispensing them into the detector line to prepare the sample mixture (1010). According to embodiments of the alternative measurement sequence 1000, the expected concentration (E) can determine how the step of preparing of the sample mixture (1010) is carried out so as to reproducibly generate appropriate response data. Appropriate response data, plotted in the form of optical density v. time generally resembles a data curve such as that shown in FIG. 21. With regard to the preparation of the sample, the expected concentration range as determined above can be utilized to determine the order in which the components of the sample are delivered to the sample/detector line. In a preferred embodiment, the order of sample constituents within the sample line comprises first carrier, then use composition, then diluent (if used), then acid (if used), and then reagent, however, generally any order can be used.

Figure 11:
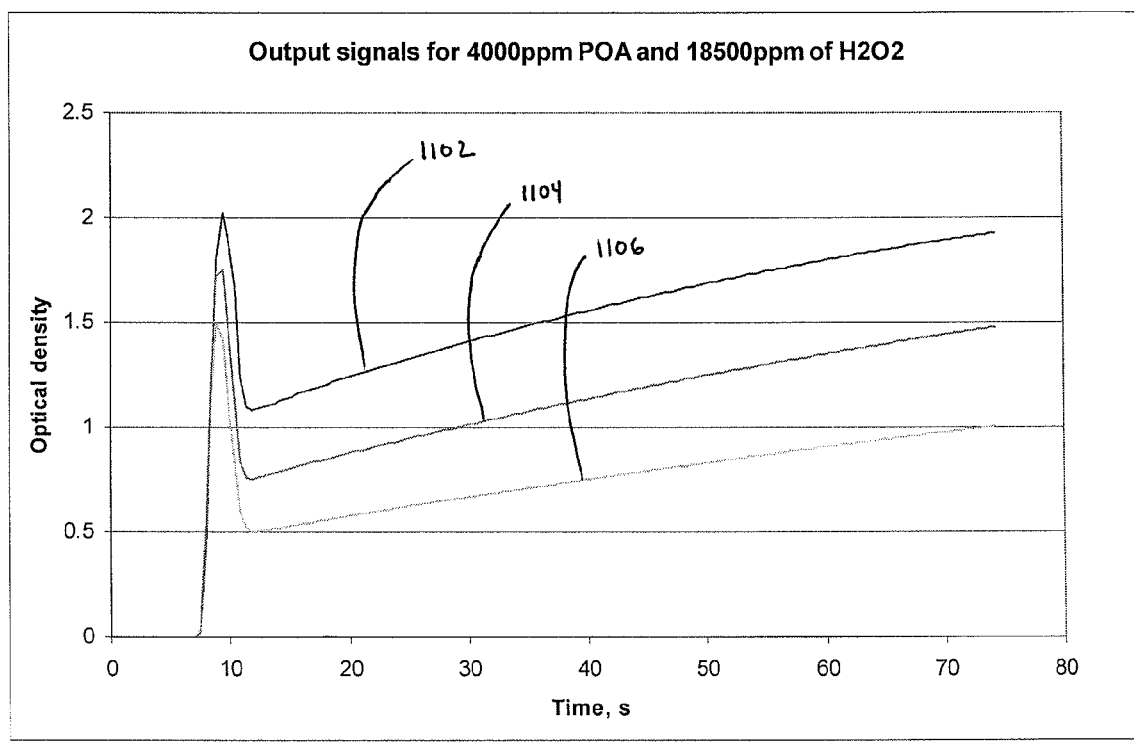
FIG. 11 is a plot of optical density versus time for a plurality of samples prepared having different barrier volumes.

Moreover, the expected concentration range can be used to determine the volumes of each of the constituents of the sample. For example, in the optical analysis of a use composition containing peracid and peroxide in high concentrations, the creation of the triiodide complex can exceed the detection capabilities of the optical sensor. That is, the sensor may not be sensitive enough to detect light passing through the reacted sample, or alternatively the detector can become saturated. In either case, appropriate response data cannot be collected and the monitor will not be capable of producing an accurate concentration reading. To prevent saturation issues, the sample can be prepared such that the collected absorbance values are well within the operating range of the detector. Such preparation can include diluting the use composition by varying the barrier volume of diluent, e.g. water, between the use composition and reagents. For example, FIG. 11 illustrates the effect of varying the barrier volume on the response data collected from three samples 1102, 1104, 1106. Each of the samples 1102, 1104, 1106 comprised a use composition having a peracid concentration of 4000 ppm and a peroxide concentration of 18500 ppm. In the first sample 1102, the barrier volume comprised 200 microliters of water. In the second sample 1104, the barrier volume comprised 250 microliters of water. And in the third sample 1106, the barrier volume comprised 300 microliters. As can be seen, the altering of the barrier volume merely vertically shifted the response data. If, for example, a monitor includes an optical detector that saturates, i.e. is inoperable, at optical densities above 1.0, embodiments of the invention would need to take precautions when preparing sample so that the response data curve does not exceed an optical density of 1.0. In such a case, where the expected concentration range would result in response data displaying curves such as curve 1104 or above, the step of preparing the sample could be modified to increase the barrier volume, thus lowering the response data curve to the range of curve 1106 which provides response data below the saturation value of the detector. While this is but one example of how the preparation step may depend upon the expected concentration range E, one of ordinary skill in the art can appreciate many further situations which similarly depend upon the expected concentration range.

Figure 12A:
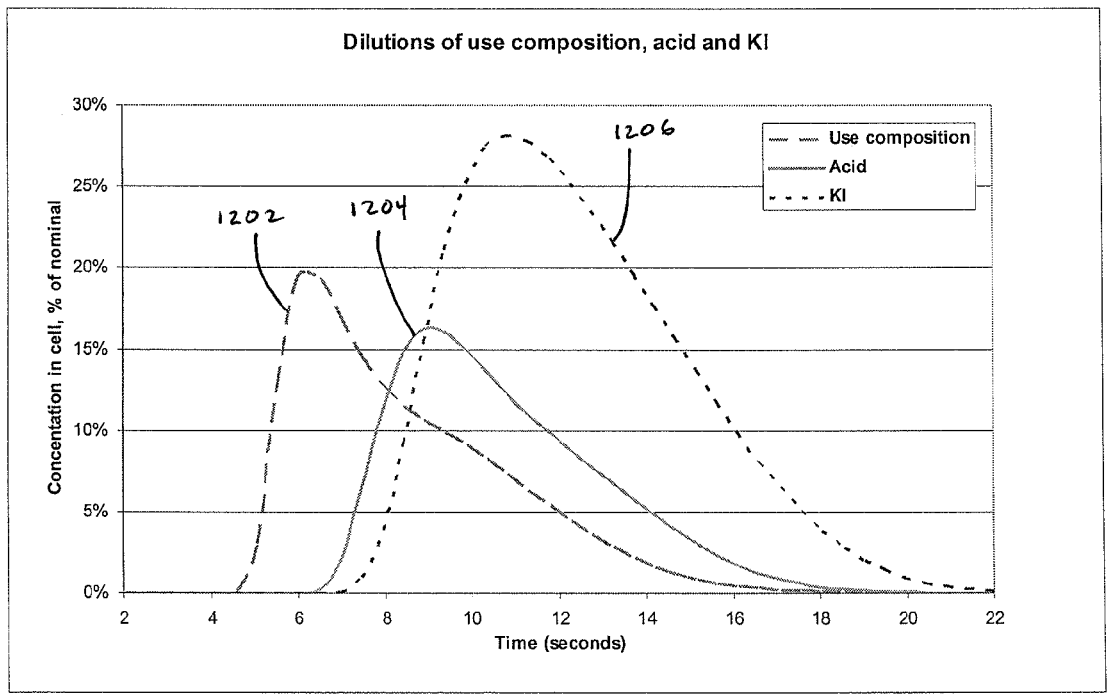
FIGS. 12A and 12B are plots of concentration versus time and concentration ratio versus time, respectively, indicating the mixing profile of a sample solution according to some embodiments.
Figure 12B:
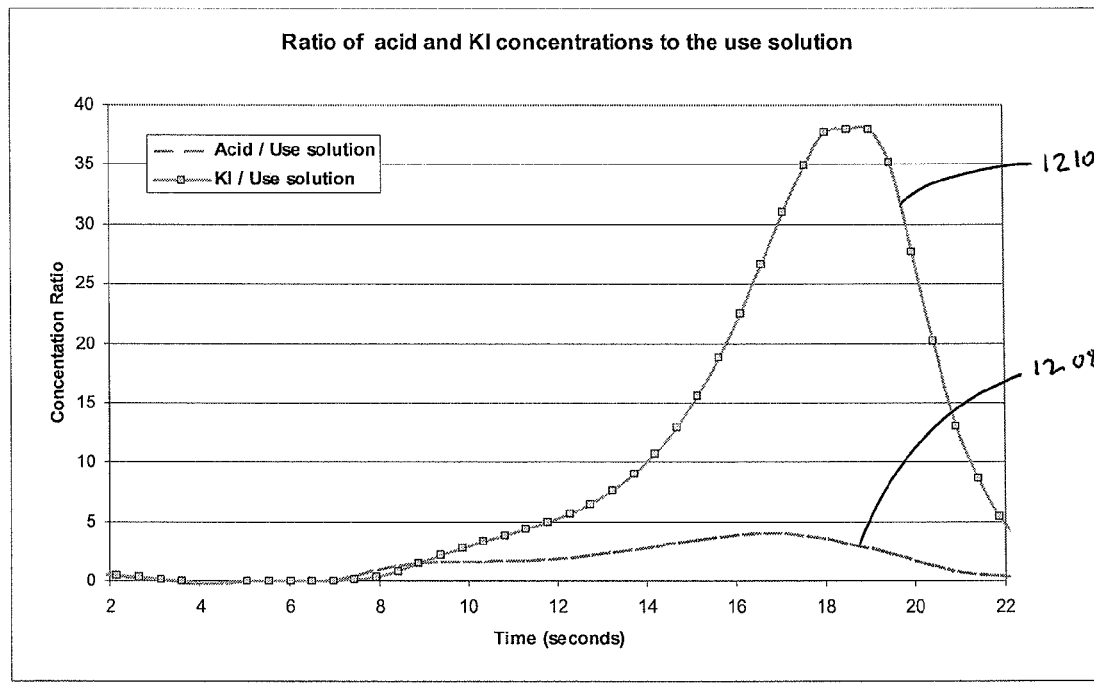
Figure 13:
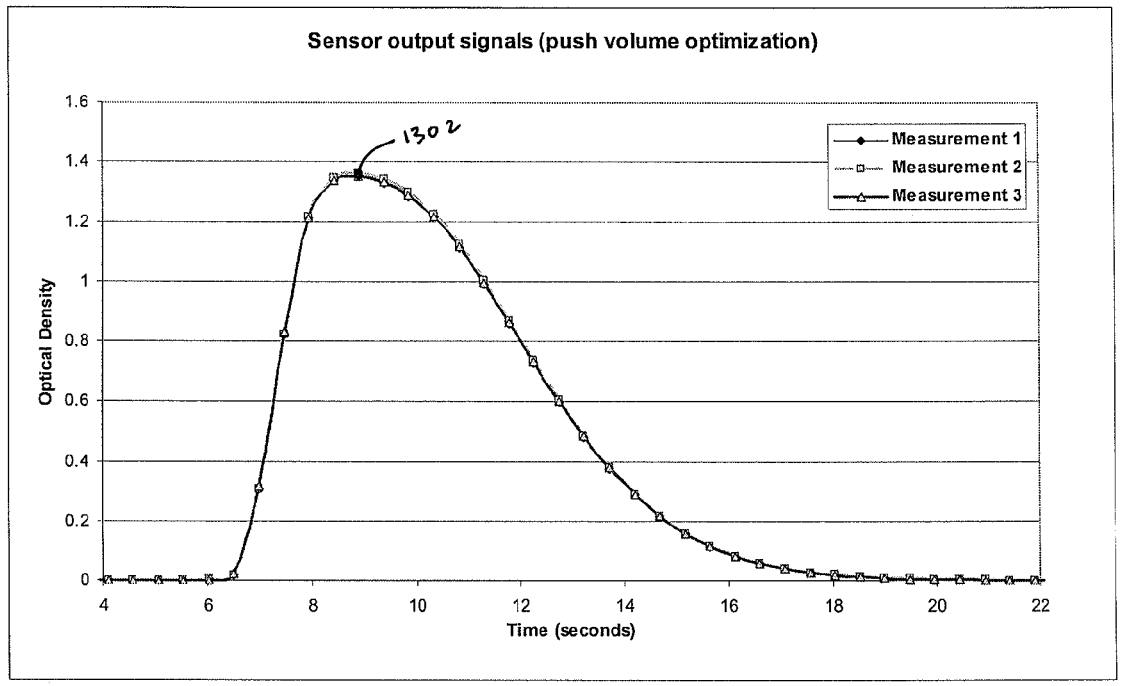
FIG. 13 is a plot of optical density versus time of a plurality of samples pushed through the detector line.

In some embodiments, during the step of preparing the sample (1010) the sample can be mixed. The sample can be mixed prior to delivery or as it is delivered to the detector. Embodiments using a laminar or non-turbulent flow mixer, such as those described above, provide a mixing profile within the mixer/detector line. For example, the mixing profile of FIG. 12A indicates concentrations of sample components with respect to time as viewed from a single location along the detector line, e.g. at a measurement location. Given that the flow rate through the detector line is known and generally constant, the graph readily translates into a plot of concentrations within the detector as a function of time. Thus, the mixing profile represents the concentrations of each sample component at any given time within the detector. In this example, a volume of use composition can be seen to bleed back into a volume of acid and reagent as indicated by use composition, acid, and reagent curves 1202, 1204, 1206. That is, for example, the relative concentrations of the sample at a detector location on the mixing profile corresponding to 14 seconds from when the pump was activated are approximately: 2% use composition, 5% acid, and 18% reagent (KI in this case). The remaining 75% of the sample at this location comprises carrier fluid or a diluent. Percent concentrations as shown in FIG. 12A are the percentage of nominal concentration delivered to the inputs from corresponding lines. FIG. 12B shows data from FIG. 12A in another form, i.e. as a ratios of (1) acid volume relative to volume of use composition 1208 and (2) reagent (e.g. KI) volume relative to volume of use composition 1210.

According to the present invention, embodiments of methods and devices for determining the concentrations of one or more use compositions undergoing kinetic reactions include obtaining response data from a sample over time. Thus, in the alternative measurement sequence 1000 of FIG. 10, the step of collecting response data (1012) can comprise delivering the sample mixture to the optical cell such that a desired measurement location along the mixing profile is positioned within the optical cell. In such embodiments, the measurement location should be selected to provide appropriate response data.

Figure 14:
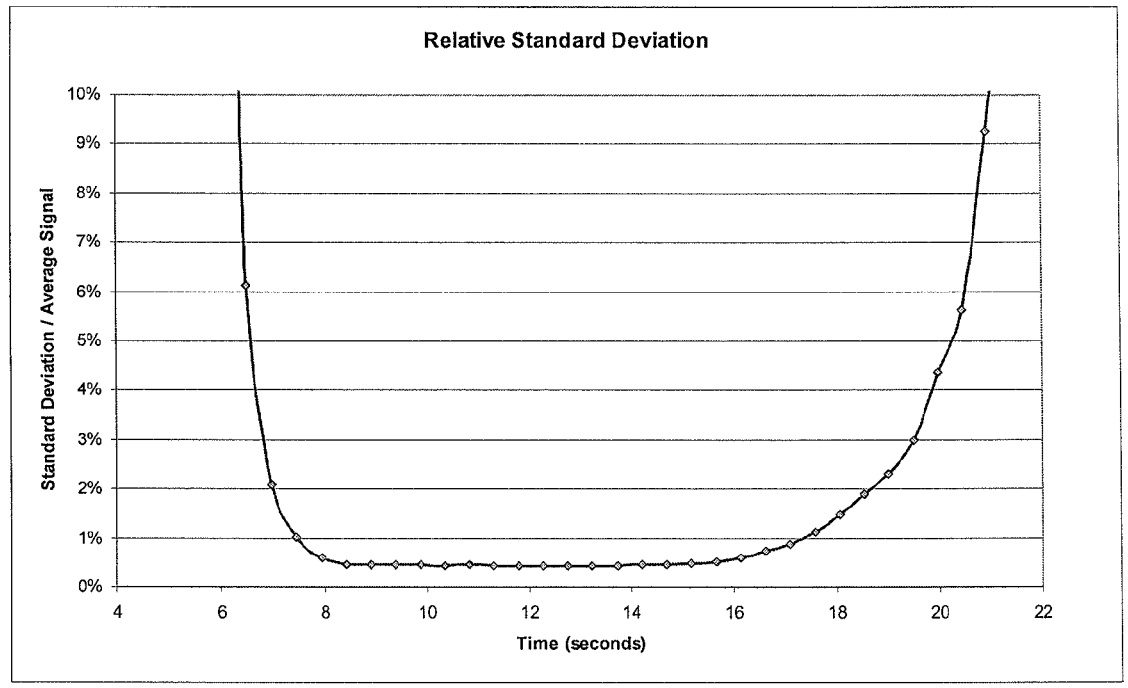
FIG. 14 is a plot of the standard deviations of the recorded optical densities of the samples of FIG. 13.

FIGS. 12A-14 can be used to illustrate one way to determine an appropriate lag time, i.e. the determination of when to stop the sample flow such that the desired measurement location is within the optical cell. It is generally preferable to have an excess of reagent in comparison with use composition so the reaction of the use composition can be fully carried out. With respect to FIGS. 12A and 12B it can be seen that, in the embodiment of the monitor used to generate that particular mixing profile, an excess of reagent occurs at approximately 9 seconds. Accordingly, this time approximately corresponds with the maximum point 1302 shown in FIG. 13, which represents the optical density v. time plot of a plurality of samples pushed straight through the detector line. In addition, FIG. 14 shows the standard deviations of the recorded optical densities of the samples of FIG. 13. In some preferred embodiments, the measurement location is selected at approximately the local minimum of the standard deviation (FIG. 14) and at a point along the push volume optical density curve (FIG. 13) so as to allow for operation within the dynamic range of the optical sensors. Thus in some embodiments, the measurement location is selected at approximately 11 seconds from the start of pumping of the sample through the detector line. This is the point from which the time derivative absorption values start, i.e. corresponding with the start of the linear portions of the response curves of each sample 1102, 1104, 1106 as seen in FIG. 11. For other embodiments and for different concentration levels of active components within the use composition, different pumping time (lag time) can be selected. In some embodiments, two conditions should be met to select an acceptable lag time: (1) the relative standard deviation for output signals should be less than a predetermined limit (for example, less than 1%); and (2) the ratios of the acid and the reagent (e.g. KI) concentrations to the use composition concentration should not exceed a ratio set for the nominal solutions. For example, from FIG. 12B, it can be seen that at 17 seconds for nominal concentrations, the acid-to-use composition ratio is approximately 4 and the reagent-to-use composition ratio is approximately 31. From FIG. 14, it can be seen that the relative standard deviation at this time (17 seconds) is less than 1%. Thus, at 17 seconds, in this embodiment, the analytical device can work with a use composition having component concentrations four times greater than those in the use composition than was set for the nominal solutions. It will be the nominal ratio for acid and an excess of reagent as required.

The selection of a measurement location along a mixing profile to provide reproducible appropriate response data can be facilitated by providing controlled laminar flow mixing of the sample. Controlled laminar flow mixing is generally accomplished by providing for repeatable laminar mixing of the components of the sample. To provide for such controlled mixing, it is generally desirable that the laminar flow mixer be maintained at a constant temperature along its entire length as uneven heating of the sample within the mixer can lead to unpredictable, and undesirable mixing. Thus, embodiments of the temperature regulated optical sensors described below may be preferable for carrying out some methods according to embodiments of the invention.

The absorbance of the analyte utilized in this system increases as the analyte concentration increases. At low and high analyte concentration the absorption reaches a minimum or maximum that negatively affects the accuracy of the measurement. Most analytes have an absorbance curve over a range of wavelengths that allows for light sources with these specific wavelengths to be utilized.

Once detector 222 receives the sample mixture, processor 212 collects the response data from detector 222 (1012). In the case of an optical detector, the response data is the measured change in the optical response of the detector over time. In some embodiments, detector 222 measures response data by measuring the color change (e.g., absorbance or transmittance) of the sample solution within detector 222 as a function of time. In other words, the voltage response of detector 222 as a function of time corresponds to the amount of light transmitted through the sample mixture and hence the color the of the sample mixture as the chemical reaction progresses. The response data is indicative of the concentrations of peracid and hydrogen peroxide in the use composition.

Once processor 212 has collected the response data (1012), processor 212 determines the concentrations of peracid and/or hydrogen peroxide in the use composition based on the response data (1014), and according to the expected concentration E. For relatively low concentrations, this process has described in more detail with respect to FIGS. 3A-3D and FIG. 4. With respect to higher concentrations, the process has been described below. The measurement sequence is then complete (1016). Processor 212 may then wait for the next monitoring interval or for a user request and repeat the sequence 240 with a new sample of use composition.

After detector 222 collects the response data, use composition monitor 200 may be rinsed and readied for the next monitoring interval (not shown). This may occur either simultaneously with or after the concentrations of peracid and hydrogen peroxide in the use composition are determined. Rinsing may also take place prior to preparation of the blank sample to ensure adequate rinsing of the use composition monitor 200. The sample line 219A may also be flushed with the use composition shortly or immediately prior to preparation of the sample mixture to ensure that the measurements are taken using the freshest use composition and thus help to ensure results that accurately reflect the current concentrations of peracid and/or peroxide in the use composition.

Table 1 shows one example implementation of the measurement sequence shown in FIG. 2. However, it shall be understood that Table 1 shows but one example of many possible measurement sequences, and that the invention is not limited to this particular implementation.

TABLE 1

Example Measurement Sequence

Start
Verify water valve is closed
Verify sample line valve is closed
Select mixer/detector line
    Dispense 2800 microliters
Select carrier line
    Aspirate 2800 microliters carrier
Select mixer/detector line
    Dispense 2900 microliters
Select carrier line
    Aspirate 1900 microliters
Select KI line
    Aspirate 250 microliters
Select mixer/detector line
    Dispense 250 microliters
Select acid line
    Aspirate 100 microliters
Select mixer/detector line
    Dispense 50 microliters
Select waste line
    Dispense 150 microliters
Select mixer/detector line
    Dispense 1500 microliters
Collect detector response with reagent blank
Open sample valve
Select carrier line
    Aspirate 2800 microliters
Select mixer/detector line
    Dispense 2800 microliters
Select carrier line
    Aspirate 1900 microliters
Select KI line
    Aspirate 250 microliters
Select mixer/detector line
    Dispense 250 microliters
Select acid line
    Aspirate 100 microliters
Select mixer/detector line
    Dispense 50 microliters
Select waste line
    Dispense 2800 microliters
Select carrier line
    Aspirate 1000 microliters
Select sample line
    Aspirate 500 microliters
Select waste line
    Dispense 1000 microliters
Select sample line
    Aspirate 500 microliters
Select waste line
    Dispense 2800 microliters
Select carrier line
    Aspirate 1800 microliters
Select sample line
    Aspirate 450 microliters
Select mixer/detector line
Close sample valve
    Dispense 1500 microliters
Collect response data with sample mixture
Select carrier line
    Aspirate 1000 microliters
Select mixer/detector line
    Dispense 2800 microliters
Select carrier line
    Aspirate 2800 microliters
Select mixer/detector line
    Dispense 2900 microliters TABLE 1-continued Example Measurement Sequence Select carrier line
    Aspirate 2000 microliters
Done Table 2 shows one example implementation of the measurement sequence shown in FIG. 10. However, it shall be understood that Table 2 shows but one example of many possible measurement sequences, and that the invention is not limited to this particular implementation.

TABLE 2

Example Alternative Measurement Sequence

I. Rinse detector with water.

Rotate stream selector to detector position.
Take syringe pump out of sleep mode.
Empty the syringe at a speed of 200 microliters a second.
Take vacuum pump out of sleep mode.
Rotate stream selector to water position.
Aspirate the syringe full at a speed of 100 microliters a second.
Put vacuum pump in sleep mode.

II. Perform zero measurement.

Rotate stream selector to detector position.
Pump (Push Vol) microliters out of the syringe at a speed of 100 microliters a second.
Zero unit during (Lag Time) + (Measure Time).

III. Flush sample line.

Turn on the sample valve.
Take vacuum pump out of sleep mode.
Rotate stream selector to water position.
Aspirate [(Push Vol) − 600] microliters to the syringe at a speed of 100 microliters a second.
Put vacuum pump in sleep mode.
Turn the sample valve off after the sample rinse time expires.
Rotate stream selector to sample position.
Aspirate 600 microliters to the syringe at a speed of 50 microliters a second.
Rotate stream selector to drain position.
Pump 600 microliters out of the syringe at a speed of 200 microliters a second.
Rotate stream selector to sample position.
Aspirate 600 microliters to the syringe at a speed of 50 microliters a second.
Rotate stream selector to drain position.
Pump 600 microliters out of the syringe at a speed of 200 microliters a second.
Rotate stream selector to sample position.

IV. Dispense sample to the detector channel.

Aspirate 600 microliters to the syringe at a speed of 50 microliters a second.
Rotate stream selector to drain position.
Pump 100 microliters out of the syringe at a speed of 100 microliters a second.
Rotate stream selector to detector position.
Pump (Sample Vol) microliters out of the syringe at a speed of 100 microliters a second.
Rotate stream selector to drain position.
Empty the syringe at a speed of 200 microliters a second.

V. Partially fill syringe with water.

Take vacuum pump out of sleep mode.
Rotate stream selector to water position.
Aspirate [2400 − (Barrier Vol) − (KI Vol) − (HOAC Vol)] microliters to the syringe at a speed of 100 microliters a second.
Put vacuum pump in sleep mode.

VI. Aspirate KI Volume

Rotate stream selector to KI position.
Aspirate [(KI Vol)] microliters to the syringe at a speed of 50 microliters a second.

TABLE 2-continued

Example Alternative Measurement Sequence

VII. Aspirate HOAC Volume

Rotate stream selector to HOAC position.
Aspirate [(HOAC Vol)] microliters to the syringe at a speed of 50 microliters a second.

VIII. Aspirate Barrier Volume

Take vacuum pump out of sleep mode.
Rotate stream selector to water position.
Aspirate [(Barrier Vol)] microliters to the syringe at a speed of 50 microliters a second.
Put vacuum pump in sleep mode.

IX. Push solution to detector

Rotate stream selector to detector position.
Pump (Push Vol) microliters out of the syringe at a speed of 100 microliters a second.

X. Perform measurement

Take a reading during (Lag Time) + (Measure Time).

XI. Rinse detector channel

Empty the syringe at a speed of 200 microliters a second.
Take vacuum pump out of sleep mode.
Rotate stream selector to water position.
Aspirate the syringe full at a speed of 100 microliters a second.
Put vacuum pump in sleep mode.
Rotate stream selector to detector position.
Empty the syringe at a speed of 200 microliters a second.

XII. Rinse sample line

Take vacuum pump out of sleep mode.
Rotate stream selector to water position.
Aspirate the syringe full at a speed of 100 microliters a second.
Put vacuum pump in sleep mode.
Rotate stream selector to sample position.
Pump 2000 microliters out of the syringe at a speed of 200 microliters a second.
Rotate stream selector to drain position.
Empty the syringe at a speed of 200 microliters a second.

XIII. Prepare unit for next measurement

Take vacuum pump out of sleep mode.
Rotate stream selector to water position.
Aspirate the syringe full at a speed of 100 microliters a second.
Put vacuum pump and syringe pump in sleep mode.
Turn on the H2O valve.
Turn the H2O valve off after the water rinse time expires.
Return to step one on reinitiating measurement procedure.

The measurement sequence of Table 2 has been described with reference to a peracid and peroxide use composition monitor having a syringe volume of 2400 microliters. The variable "Push vol" as used above, can represent the volume of liquid pushed through the detector line prior to a measurement or zeroing of the system. This push volume can be selected to deliver mixed use composition into the optical cell at a measurement location along the mixing profile. In some embodiments, this measurement location can be a location along the mixing profile where there is a maximum of reagent (e.g. KI) and relative standard deviation of optical cell readings is at a minimum. The variables "KI Vol," "HOAC Vol," and "Sample Vol" represent, respectively, the volumes of reagent (e.g. KI), acid (e.g. acetic acid, if applicable), and use composition delivered through the detector line during a measurement sequence. The variable "Barrier Vol" can represent the volume of barrier liquid (e.g. water) separating the reagent and acid (if applicable) from the use composition as the measurement sequence starts. Accordingly, in some embodiments, the mixing profile of the measurement sequence can depend upon the values selected for these variables. Timing variables used in Table 2 include "Lag Time" and "Measurement Time." The "Lag Time" represents the time needed to deliver the sample through the detector line such that the measurement location along the mixing profile is stopped within the optical cell. Data collected from the optical cell during the Lag Time is generally not used in performing a measurement calculation. The "Measurement Time" represents the duration for which the measurement location is stopped within the optical cell. Data collected from the optical cell during the Measurement Time is used to perform the measurement calculation. Values (volume and/or time) to replace the variables used above can be selected based upon a variety of factors, including but not limited to, the expected concentration range of the use composition.

Use composition monitor 200 determines the concentrations of peracid and/or hydrogen peroxide in the use composition using a kinetic assay procedure. This is accomplished by exploiting the difference in reaction rates between peracid and hydrogen peroxide when using, for example, a buffered iodide reagent to differentiate peracid and hydrogen peroxide concentrations when both these analyte compounds are present in the use composition. Use composition monitor 200 may also determine the concentrations of peracid and/or hydrogen peroxide in the presence of other additional ingredients, such as acidulants, one or more stabilizing agents, nonionic surfactants, semi-polar nonionic surfactants, anionic surfactants, amphoteric or ampholytic surfactants, adjuvants, solvents, additional antimicrobial agents or other ingredients which may be present in the use composition.

In a use composition including hydrogen peroxide and a peracid such as peroxyacetic acid, a buffered iodide changes color as it is oxidized by both the peroxyacetic acid and the hydrogen peroxide to form triiodide ion. However, as the peroxyacetic acid and the hydrogen peroxide in the use composition compete for the available iodide ions, reaction with the peroxyacetic acid proceeds at a faster rate than the reaction with the hydrogen peroxide, as shown in the following equations:

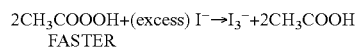

$$2CH_3COOOH + (excess)\ I^- \rightarrow I_3^- + 2CH_3COOH\ \text{FASTER}$$

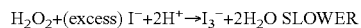

$$H_2O_2 + (excess)\ I^- + 2H^+ \rightarrow I_3^- + 2H_2O\ \text{SLOWER}$$

This difference in reaction rates may be exploited to differentiate peracid and hydrogen peroxide concentrations when both these analyte compounds are present in the use composition. An example reaction is described below and the results illustrated in FIGS. 3A-3D. It shall be understood, however, that the example below is for illustrative purposes only and that the invention is not limited to the particular reaction chemistry described in the example below, and that the invention is not limited in this respect.

EXAMPLE

A buffered potassium iodide reagent was prepared by adding 0.489 g KI to 50 ml of 2% KHP (potassium acid phthalate) and diluting to 100 ml with deionized water. Other suitable buffers would also provide adequate buffering. For example, phosphate-based buffer prepared from potassium dihydrogen phosphate and dibasic sodium phosphate could be used to buffer the reagent to a pH of approximately 5.0 to 6.5. The iodide solution was tested over the concentration range of 0.025 Molar to 0.075 Molar iodide. It shall be understood that other buffer solutions or an unbuffered iodide solution may also be used depending upon the concentration of acid within the peracid and peroxide in the solution, as will be understood by those of skill in the art.

The samples were tested at room temperature to determine absorbance at 365 nm over times ranging from 0 to 114 seconds. In these experiments, absorbance data were acquired using a Cary 100 Bio UV-Visible scanning spectrophotometer (Varian, Inc., Palo Alto, Calif.). The results are shown in Table 3 and plotted in FIGS. 3A-3D.

TABLE 3

| ppm POAA in cell | Total ppm perox in sample |
|---|---|
| 0.5 | 0.39 |
|  | 5.39 |
|  | 10.39 |
|  | 20.39 |
|  | 35.39 |
| 1 | 0.77 |
|  | 4.77 |
|  | 9.77 |
|  | 9.77 |
|  | 19.77 |
|  | 34.77 |
| 2 | 1.54 |
|  | 5.54 |
|  | 10.54 |
|  | 20.54 |
|  | 35.54 |
| 4 | 3.08 |
|  | 7.08 |
|  | 12.08 |
|  | 22.08 |
|  | 37.08 |

The absorbance vs. time plotted in FIG. 3A shows a substantially linear increase, which resulted from the reaction of the hydrogen peroxide in the samples with the iodide ion supplied by the reagent KI solution. As shown in FIG. 3B, the absorbance at t=0 ($A_0$) remained constant as the concentration of peroxide in the sample increased, while the plot of $A_0$ vs. concentration of POAA in FIG. 3C shows a linear relationship, which suggested that $A_0$ is proportional to the concentration of POAA and apparently independent of the concentration of hydrogen peroxide. Referring to FIG. 3D, the slope of the rate of absorbance, $A_r$, vs. time curve is proportional to the concentration of peroxide in the sample, and is apparently independent of the concentration of POAA in the sample.

This Example illustrates that at room temperature, the initial absorbance at 365 nm of the triiodide complex, measured at time=0 seconds, $A_0$, is independent of the concentration of hydrogen peroxide in the use composition. The rate of the change in absorbance of the triiodide complex for time>0 seconds, $A_r$, is indicative of the concentration of hydrogen peroxide. Further, increasing the hydrogen peroxide concentration increases the rate of increase of the absorbance of the triiodide complex, $A_r$. This relationship demonstrates that: (1) the initial absorbance $A_0$, is dependent on the peroxyacetic acid concentration and independent of the hydrogen peroxide concentration; and (2) the rate of increase of the absorbance, $A_r$, is dependent on the concentration of hydrogen peroxide and independent of the peroxyacetic acid concentration. The related and competing reactions with the triiodide complex demonstrate that it is possible to simultaneously measure the concentration of peroxyacetic acid and the concentration of hydrogen peroxide in a sample of the use composition using a kinetic assay procedure.

Figure 4:
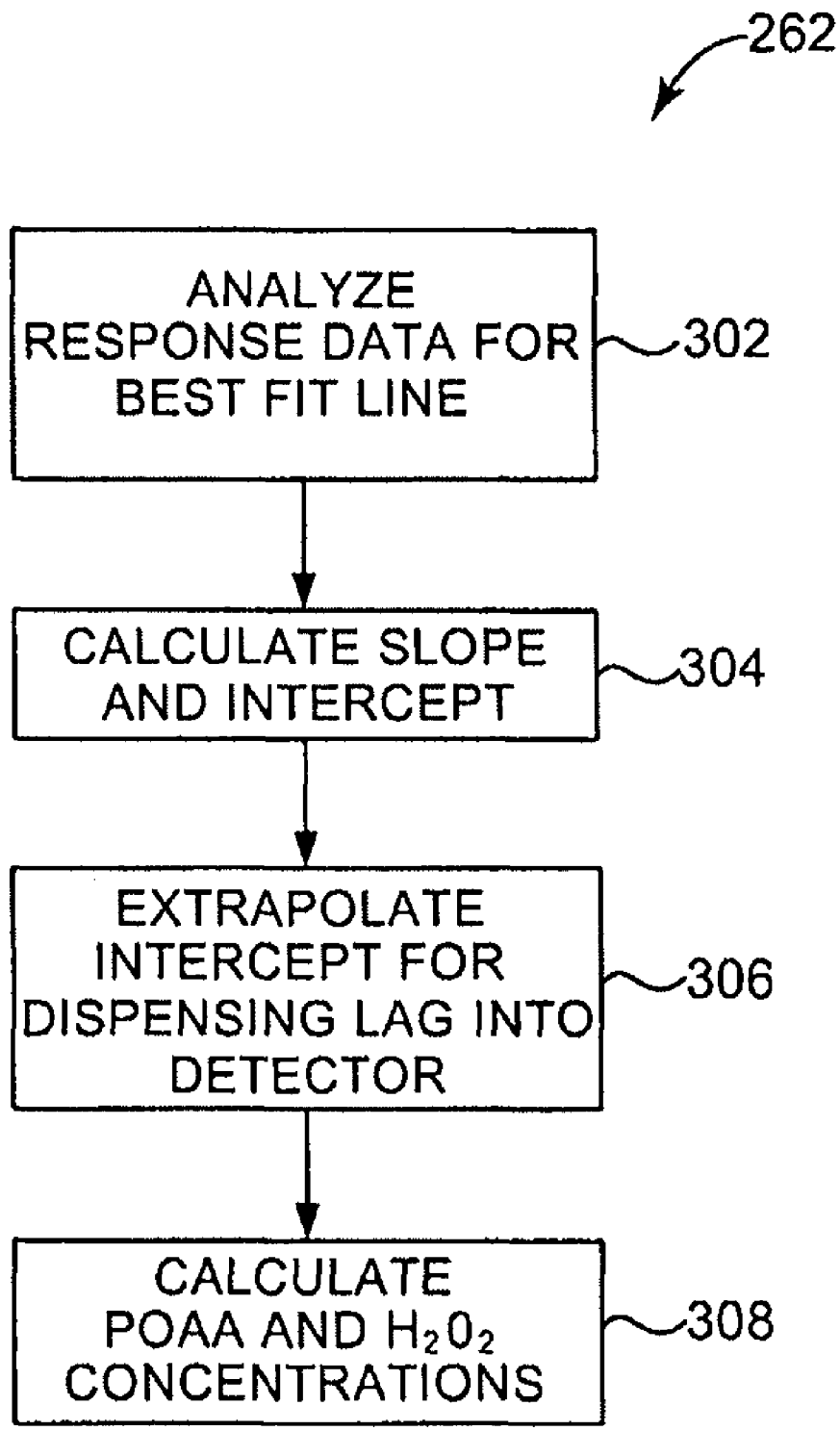
FIG. 4 is a flowchart illustrating a procedure by which a processor determines the concentrations of peracid and hydrogen peroxide from response data.

FIG. 4 is a flowchart illustrating the procedure by which processor 212 determines the concentrations of peracid and hydrogen peroxide from response data obtained by detector 222. As discussed above, the response data, when plotted as absorbance versus time, reveals that the absorbance at t=0 ($A_0$) is proportional to the concentration of peracid in the use composition. In addition, the rate (slope) of absorbance, $A_r$, vs. time is proportional to the concentration of peroxide in the sample.

The absorbance values at each point in time, $A_t$, are determined by the following equations:

$$A_t = -\log_{10} V_t / V_0,$$

where $V_t$ is the voltage response of the detector and $V_0$ is the voltage response of the detector measured with the reagent blank.

When the response data has been collected and the absorbance values as a function of time have been calculated, processor 212 analyzes the response data to determine the relationship that best fits the response data (302). For example, processor 212 may perform a polynomial regression on the response data to determine the best fit equation. The polynomial regression may be a first order equation (linear regression) or may be a higher order equation (generally non-linear but which may approximate a linear relationship over certain measurement intervals).

As is known to those of skill in the art, linear regression attempts to model the relationship between two variables by fitting a linear equation to observed data. A linear relationship is governed by the equation y=mx+b, where the m is the slope and b is the y-intercept. It shall be understood, however, that higher order equations may also be used when needed without departing from the scope of the present invention. When higher order equations the measurement interval may be adjusted so that the resulting equations approximate a linear relationship so that a slope may be approximated.

In some embodiments, the regression analysis may be performed in real time as the response data is collected. In other embodiments, the regression analysis may be performed after all of the response data has been collected.

Once the regression analysis is performed and the best fit line (or higher order equation) is found (302) the slope and the y-intercept are determined (304). In one embodiment, the y-intercept is extrapolated back (306) to account for a time lag ($t_{lag}$) which may occur between when the reagent is mixed with the diluted sample in static mixer 222 and when the sample/carrier/reagent mixture actually arrives into the detector (see 258 in FIG. 2). Because the reaction between the peracid and the reagent(s) occurs quickly (for example, within 1 second), that reaction may already be complete by the time the sample mixture arrives in the detector. Thus, there may a delay between the time that the sample mixture arrives in the detector (time $t_0$) and the time that the peracid reaction takes place (time $t_0$-$t_{lag}$). In the embodiment of FIG. 1, the time $t_{lag}$ is approximately 3 seconds, but may be anywhere from about 0.5 seconds to about 15 seconds. Since the linear relationship between absorbance and time is known, the y-intercept may be extrapolated back in time by an amount equal to $t_{lag}$ to determine the adjusted y-intercept value ($b_{adj}$) that is in some embodiments proportional to the concentration of peracid in the use composition.

Processor 212 then determines the actual concentrations of the peracid and/or the concentration of hydrogen peroxide in the use composition (308). Because the y-intercept and slope are proportional to the concentration of peracid and hydrogen peroxide, respectively, conversion factors may be determined which allow calculation of the concentrations based on knowledge of the y-intercept and slope of the linear relationship which best fits the response data. In one embodiment, processor 212 multiplies the y-intercept and slope by predetermined conversion factors to calculate the actual concentrations of peracid and hydrogen peroxide, respectively, in the use composition. The conversion factors are determined by calculating the slope and intercepts for known standard peracid and hydrogen peroxide samples and using the resulting relationships to calculate proportionality constants.

In one embodiment, the peracid conversion factor for converting the adjusted y-intercept, $b_{adj}$ into the actual concentration of peracid is 3.39 ppm peracid per absorbance unit when a 1 cm optical cell is used. The peroxide conversion factor for converting the slope, m, into the actual concentration of hydrogen peroxide is 6692 ppm per absorbance unit per second when a 1 cm cell is used. The conversion factors may be used to determine the actual concentrations of peracid and/or the concentration of hydrogen peroxide in the use composition using the following equations:

ppm peracid=$A_{t=0}$·(peracid conversion factor)= $A_{t=0}$·3.39, ppm peroxide=Slope·(peroxide conversion factor)= Slope·6692 where $A_{t=0}$ and the Slope are determined from a polynomial regression of the absorbance versus time data obtained at 365 nm. The polynomial regression may be, for example, a first order (linear) equation. The polynomial regression may also be a higher order (nonlinear) equation. It shall be understood that the above conversion factors are for exemplary purposes only, and that other appropriate conversion factors may be used depending upon the volume of sample introduced into the reaction mixture and the extent of dilution of the sample during the mixing process within the instrument, and that the invention is not limited in this respect.

In another embodiment, the actual concentrations of peracid and/or peroxide in the use composition may be determined based upon optimized higher order conversion equations. In particular, it has been recognized that a linear conversion relationship based upon a single parameter (i.e. peracid concentration=$f(A_{t=0})$ and peroxide concentration=f (slope)) does not hold for high concentrations of peracid and/or peroxide. Thus, at higher concentrations, peracid can be said to be a function of initial absorbance and slope (i.e. peracid concentration=$f(A_{t=0},$ slope)) and peroxide is a function of slope and initial absorbance (i.e. peroxide concentration=f(slope, $A_{t=0}$). In one example, a higher order conversion equations can take the following form:

ppm peracid=$[K_{1a}+K_{2a}X_m+K_{3a}Y_m+K_{4a}X_m\hat{~}(B_{1a})+ K_{5a}Y_m\hat{~}(B_{2a})+K_{6a}X_m\hat{~}(B_{3a})Y_m\hat{~}(B_{4a})]\hat{~}(B_{5a})$ ppm peroxide=$[K_{1b}+K_{2b}X_m+K_{3b}Y_m+K_{4b}X_m\hat{~}(B_{1b})+ K_{5b}Y_m\hat{~}(B_{2b})+K_{6b}X_m\hat{~}(B_{3b})Y_m\hat{~}(B_{4b})]\hat{~}(B_{5b})$ where $X_m$ is the measured initial absorbance $A_{t=0}$ and $Y_m$ is the measured slope. $K_{1a}$-$K_{6a}$ and $B_{1a}$-$B_{5a}$ are coefficients with respect to the peracid concentration. Likewise, $K_{1b}$-$K_{6b}$ and $B_{1b}$-$B_{5b}$ are coefficients with respect to the peroxide concentration. The values of each of the coefficients ($K_{1a}$-$K_{6a}$, $B_{1a}$-$B_{5a}$, $K_{1b}$-$K_{6b}$, and $B_{1b}$-$B_{5b}$) can be determined through a calibration process run prior to the operation of the optical analysis system or can be otherwise provided.

Some embodiments comprise a method for calibrating an optical analysis instrument for determination of unknown concentrations of peracid and/or peroxide. For example, some optical analysis instruments include a calibration mode, which determines the values of high order coefficients necessary for reconciling measured response data, e.g. absorption data, with actual concentration levels. In such case, a method of calibration for an optical analysis instrument can comprise setting the device in calibration mode. The method further comprises preparing a plurality of calibration solutions to be analyzed by the instrument. The instrument obtains response data comprising at least two parameters (e.g. initial absorbance and time derivative of absorbance) from the calibration solutions. An evaluation function can then be constructed with respect to each analyte. The evaluation function can be optimized such that values are determined for coefficients of the evaluation function. The coefficient values can then be stored in memory and retained for use in a conversion function such as those described above.

Figure 15:
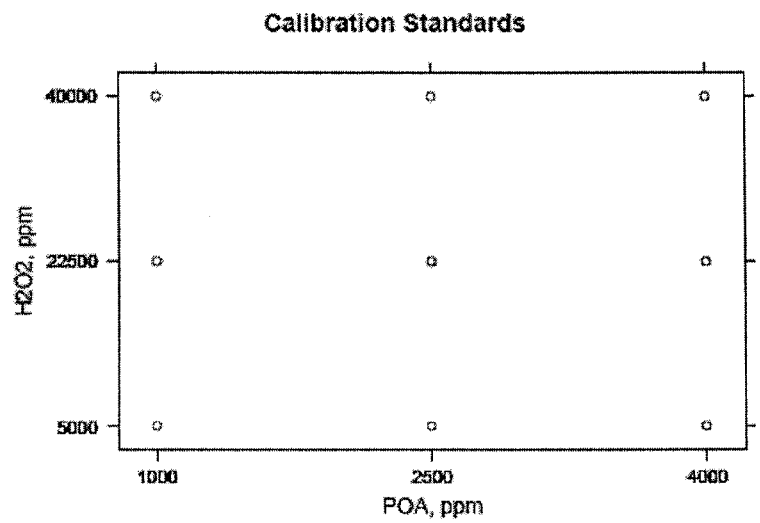
FIG. 15 is a plot indicating the concentrations of peroxide and peracid of a set of calibration solutions according to some embodiments.

FIG. 15 shows a plot of a set of calibration solutions with respect to some embodiments of the method of calibration. In this embodiment, a set of nine calibration solutions are indicated. The calibration solutions have peracid concentrations selected from the set of 1000 ppm, 2500 ppm, and 4000 ppm and peroxide concentrations selected from the set of 5000 ppm, 22,500 ppm, and 40,000 ppm. At every peracid concentration a different solution has been prepared for each of the peroxide concentrations resulting in the nine sets indicated in FIG. 15. In general, the nine solution sets have been selected to be spread out evenly across a peroxide range (5000 ppm to 40,000 ppm) and a peracid range (1000 ppm to 4000 ppm). Of course, many different combinations or arrangements of calibration solution values can be selected. For example, the calibration solutions can be prepared so as not to be evenly distributed across the peracid or peroxide ranges (e.g. in the range above, the peracid data points could be selected from the set of 1000 ppm, 1500 ppm and 4000 ppm). Moreover, in some embodiments, the number of prepared calibration solutions, and hence data points, can be selected to be more or fewer than the nine shown in this embodiment. Indeed, it is generally true that the more data points selected the more accurate the coefficients. In addition, the selected data points for the peracid range need not equal the number of selected data points for the peroxide range (e.g. 20 data points can be selected comprising four peracid concentrations and five peroxide concentrations). It is not even necessary that calibration solutions be prepared for every combination of elements of the sets of peracid and peroxide concentrations.

Figure 16:
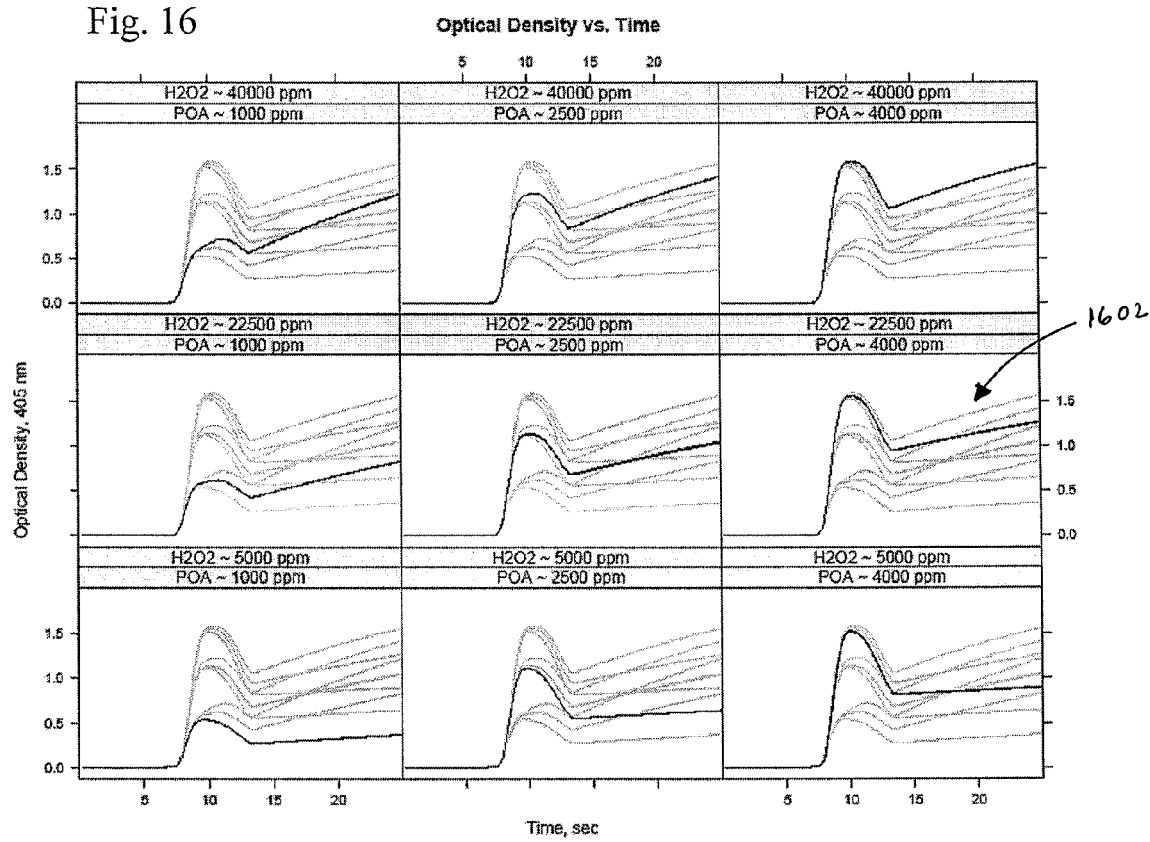
FIG. 16 is a collection of plots of optical density versus time for each of the calibration solutions indicated in FIG. 15.

Once the calibration solutions have been prepared, the optical analysis system analyzes each solution to generate corresponding response data. FIG. 16 shows exemplary plots of response data corresponding with each of the data points of FIG. 15. For example, plot 1602 shows the response data collected from the analysis of the calibration sample containing 4000 ppm peracid and 22,500 ppm peroxide. From this response data, parameter values can be determined. The parameter values selected should be parameters which are known to correspond with the concentrations of the analytes. For example, the initial absorbance and the time derivative of absorbance are known to correspond to the concentrations of peracid and peroxide.

In some embodiments, the values of the parameters of the calibration solutions can be used to calculate a high order conversion relationship between the parameters and the analyte concentrations such as that described above. To calculate the conversion relationships an optimization process can be used. For example, the optimization process can comprise constructing evaluation functions for each of the peracid and the peroxide taking the form:

$\Delta POA_i=POA_{known,i}-[K_{1a}+K_{2a}X_i+K_{3a}Y_i+K_{4a}X_i\hat{~}(B_{1a})+ K_{5a}Y_i\hat{~}(B_{2a})+K_{6a}X_i\hat{~}(B_{3a})Y_i\hat{~}(B_{4a})]\hat{~}(B_{5a})$; and $\Delta Peroxide_i=Peroxide_{known,i}-[K_{1b}+K_{2b}X_i+K_{3b}Y_i+ K_{4b}X_i\hat{~}(B_{1b})+K_{5b}Y_i\hat{~}(B_{2b})+K_{6b}X_i\hat{~}(B_{3b})Y_i\hat{~}(B_{4b})]\hat{~}(B_{5b})$, wherein $\Delta POA_i$ is the $i^{th}$ delta value of the peracid, $POA_{known,i}$ is the known concentration of the peracid of the $i^{th}$ calibration solution, $\Delta\text{Peroxide}_i$ is the $i^{th}$ delta value of the peroxide, $\text{Peroxide}_{known,i}$ is the known concentration of the peroxide of the $i^{th}$ calibration solution, $X_i$ is the value of the first parameter (i.e. the initial absorbance, $A_{t=0}$) for the $i^{th}$ calibration solution, and $Y_i$ is the value of the second parameter (i.e. the slope) for the $i^{th}$ calibration solution. Then, numerical analysis can be used to optimize the coefficients $K_{1a,b}$-$K_{6a,b}$ and $B_{1a,b}$-$B_{5a,b}$ by minimizing the sums of the squares of the normalized delta values, e.g. by minimizing the sum of $((\Delta\text{POA}_i/\text{POA}_{known,i})^2)$ for each i and the sum of $((\Delta\text{Peroxide}_i/\text{Peroxide}_{known,i})^2)$ for each i. Once coefficients have been established, they can be stored in memory for use with the above or another conversion equation.

The above described calculations, according to some embodiments, can be carried out by a processor or other local hardware. Alternatively, the calculations can be carried out by an external system.

Figure 17:
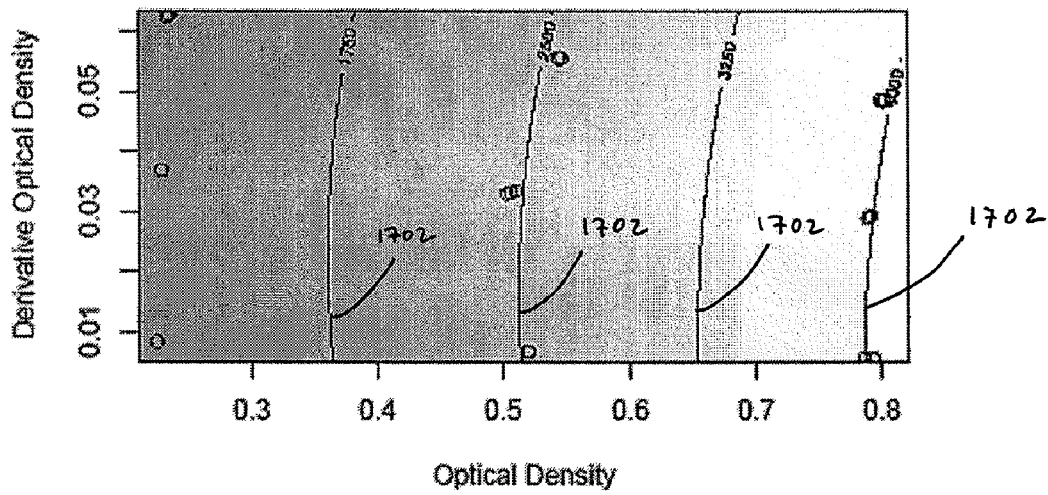
FIG. 17 is a contour plot representative of exemplary peracid concentrations as a function of measured optical density and time derivative of optical density according to some embodiments.
Figure 18:
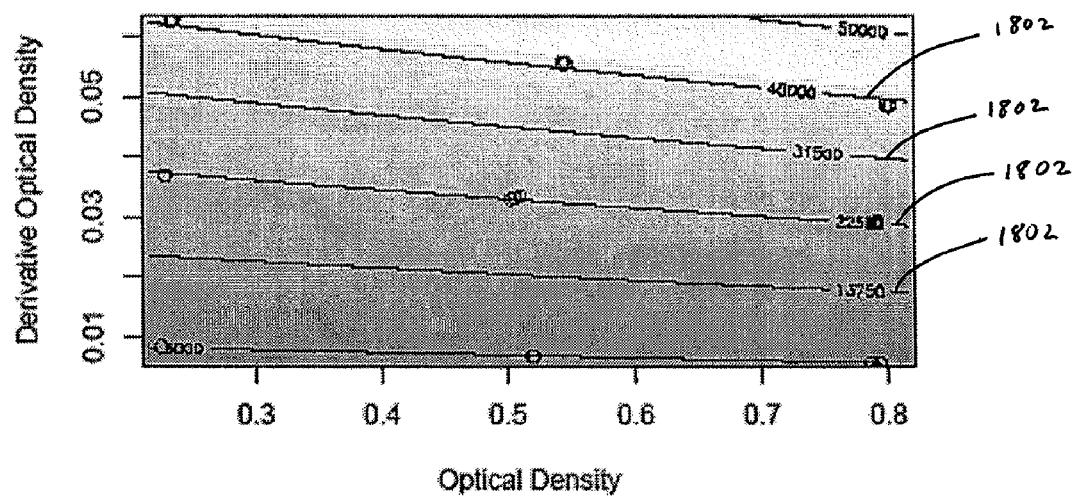
FIG. 18 is a contour plot representative of exemplary peroxide concentrations as a function of measured optical density and time derivative of optical density according to some embodiments.

FIGS. 17 and 18 show representative contour plots which illustrate how optical density (absorbance) and the slope of optical density (time derivative of absorbance) can correlate with peracid and peroxide concentrations. These contour plots were created from response data generated by calibration solutions prepared to correspond with the data points of FIG. 15 and shown in FIG. 16. As can be seen in FIG. 17, the peracid concentration (indicated by the contour lines 1702) still substantially varies according to optical density however a deviation can be seen as the derivative of optical density increases. Likewise, FIG. 18 indicates that, at these higher concentration ranges, peroxide concentration still heavily correlates with the derivative of optical density, however the slope of the contour lines 1802 indicate that the peroxide concentration varies with optical density as well.

Moreover, it should be noted that in some embodiments, the calibration solutions are prepared with reference to the expected concentration range E of the use composition. For example, for an expected peracid concentration range of 1250 ppm to 3750 ppm, and an expected peroxide concentration range of 5500 ppm to 39,000 ppm, the data points shown in FIG. 15 may be selected. By selecting data points representative of peracid and peroxide ranges which encompass the expected concentration range, the coefficients are likely to strongly represent actual coefficients at that value. However, a device need not be calibrated to encompass an entire expected range. For example, the expected range could be larger than the calibrated range. In such case, the conversion equations may still be used and are likely to provide a concentration reading that is reasonably accurate. In view of this, some systems may operate to store multiple calibrations (i.e. multiple sets of conversion coefficients or even wholly different conversion equations) such that different conversion relationships can be selected or triggered depending upon the expected concentration range or application selected.

In addition, while the above calibration methods have only been described with reference to certain embodiments illustrated herein, one should recognize that calibration methods can be used with other optical analysis systems. For example, calibration methods such as those described can be used when the optical characteristic is fluorescence, scattering, or variation of reflective index. In addition, the parameters measured and used to convert response data into analyte concentrations can include other parameters such as, for example, a derivative with respect to temperature. Moreover, any such derivatives as referenced herein can include first or higher order derivatives.

In another embodiment, the actual concentrations of peracid and/or the concentration of hydrogen peroxide in the use composition may be determined using lookup tables. In that embodiment, table entries for a plurality of possible y-intercepts would correspond to the concentration of peracid in the use composition and table entries for a plurality of possible slopes would correspond to the concentration of hydrogen peroxide in the use composition. In another embodiment, the actual concentrations of peracid and/or the concentration of hydrogen peroxide in the use composition may be determined using calibration curves or other methods known to those of skill in the art.

The concentrations of peracid and/or the concentration of hydrogen peroxide in the use composition may be used as feedback to control the concentration of peracid in the use composition. For example, the concentration of peracid typically must be maintained within a certain range, or satisfy at least a minimum threshold concentration (the minimum peracid threshold concentration), in order to ensure adequate disinfecting and/or satisfy governmental regulations. As another example, the concentration of hydrogen peroxide must be kept below a maximum threshold concentration (the maximum peroxide threshold concentration). The maximum peroxide concentration in a reuse system is set by the filler manufacturer. This value is based on the maximum level of peroxide in the solution that can be rinsed from the bottle leaving behind less than the residual hydrogen peroxide in the bottle, which is an FDA requirement. Once the concentration exceeds the peroxide threshold concentration, the use composition must be disposed of a new use composition made.

The peracid and/or peroxide concentrations may be used in any of several ways. The peracid and/or peroxide concentrations may be used as an input to a network advisory system that provides notifications, reports, alarms and/or advisory information to a field service provider, a local or on-site monitoring site or a centralized local or remote management system. The concentration information may be used to generate reports concerning the peracid and/or peroxide concentrations of the use composition at or over various points in time. The concentration information may be used to generate notifications, alarms and/or reports indicative of either a below threshold peracid concentration or an above threshold peroxide concentration. Such notifications, alarms and/or reports may include audible alarm(s), visual alarm(s) or electronically generated alarm(s), e-mails, pages, text messages, cell phone communications, scripts, etc. The alarms and/or reports may be sent to a remote monitoring site, an on-site monitoring computer, a technician and/or a field service provider. The notifications, reports and/or alarms may provide information that maintenance, service or repair should be provided at the monitored facility, and may also provide information as to the type of maintenance, service or repair, repair history, and/or advisory information designed to aid the technician or field service provider. As another example, the peracid and/or peroxide concentrations may be used to control operation (e.g., shutting down) of a use composition generator or of an end use application. Other applications of the peracid and/or peroxide concentrations may also be used.

As shown in FIG. 1, the concentration of peracid and/or the concentration of hydrogen peroxide in the use composition as determined by use composition monitor 200 are fed back to controller 100. Controller 100 may then use this concentration information to control the concentration of peracid in the use composition, and to monitor the concentration of hydrogen peroxide in the use composition to ensure it does not increase above the maximum peroxide threshold concentration.

Figure 5:
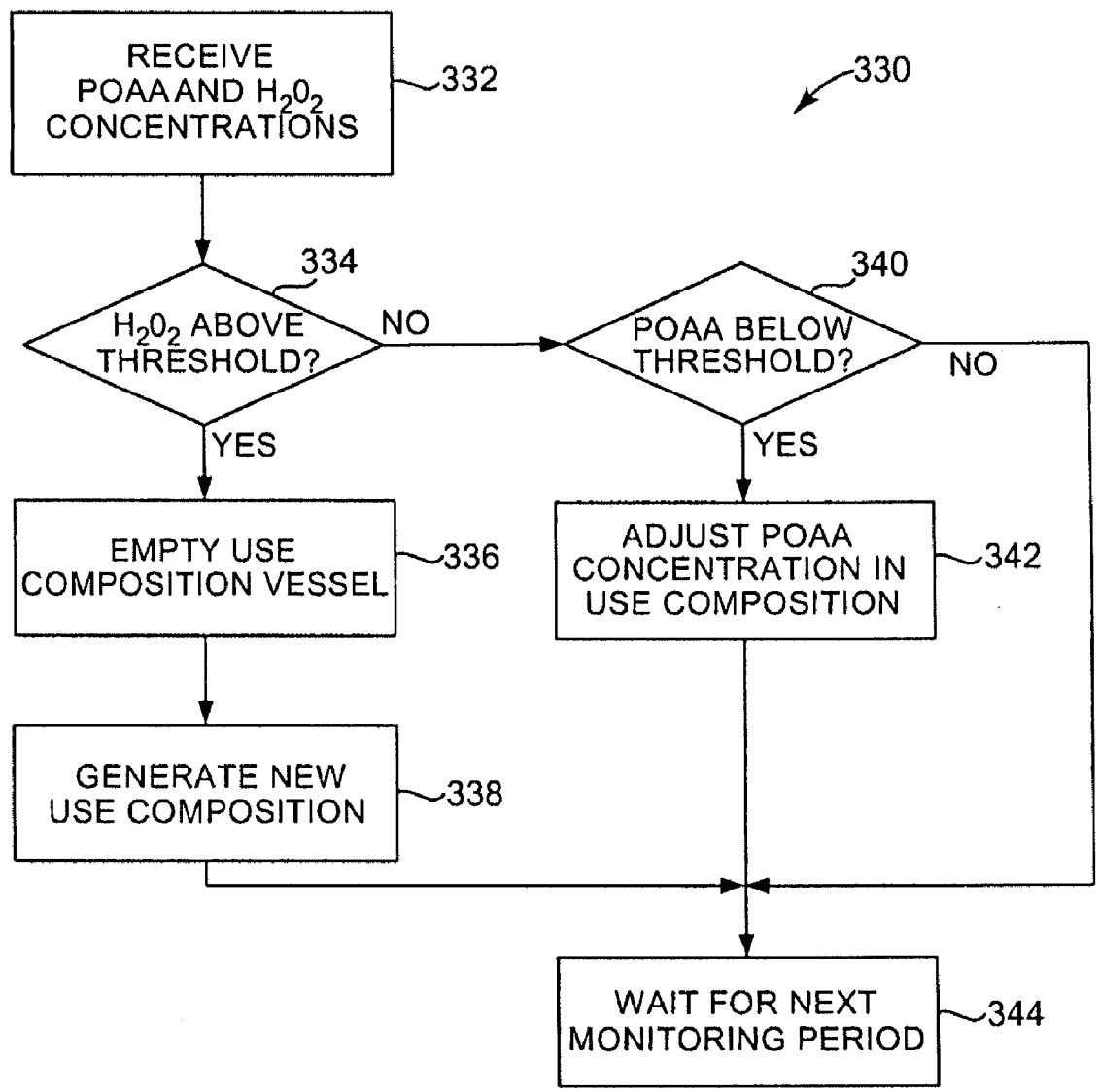
FIG. 5 is a flow chart illustrating a process by which a controller monitors and/or controls the concentrations of peracid and/or of hydrogen peroxide in the use composition.

FIG. 5 is a flow chart illustrating the process (330) by which controller 100 monitors and/or controls the concentrations of peracid and/or of hydrogen peroxide in the use composition. Controller 100 receives the peracid and/or of hydrogen peroxide concentrations (332). Controller 100 compares the received hydrogen peroxide concentration with the peroxide threshold concentration (334). If the measured hydrogen peroxide concentration exceeds the peroxide threshold concentration, controller 100 causes the use composition vessel to be emptied of the spent use composition (336). Controller 100 then controls flow of peracid and diluent into a use composition vessels (not shown) to make a new use composition (338). Controller 100 then waits for the next monitoring interval, at which point it will receive the most recently measured concentrations of peracid and/or hydrogen peroxide from use composition monitor 200 (344).

If the hydrogen peroxide concentration does not exceed the peroxide threshold concentration (334), controller 100 compares the peracid concentration in the use composition (as determined by use composition monitor 200) with the peracid threshold concentration (340). If the peracid concentration in the use composition is below the peracid threshold concentration, controller 100 may adjust the peracid concentration in the use composition until it satisfies the peracid threshold concentration (342). To do this, controller 100 may control valves on the peracid concentrate holding tank and/or diluent holding tank such that a given amount of peracid and/or diluent is added to the use composition in use composition vessel, causing a resultant increase in the concentration of peracid in the use composition.

Figure 6:
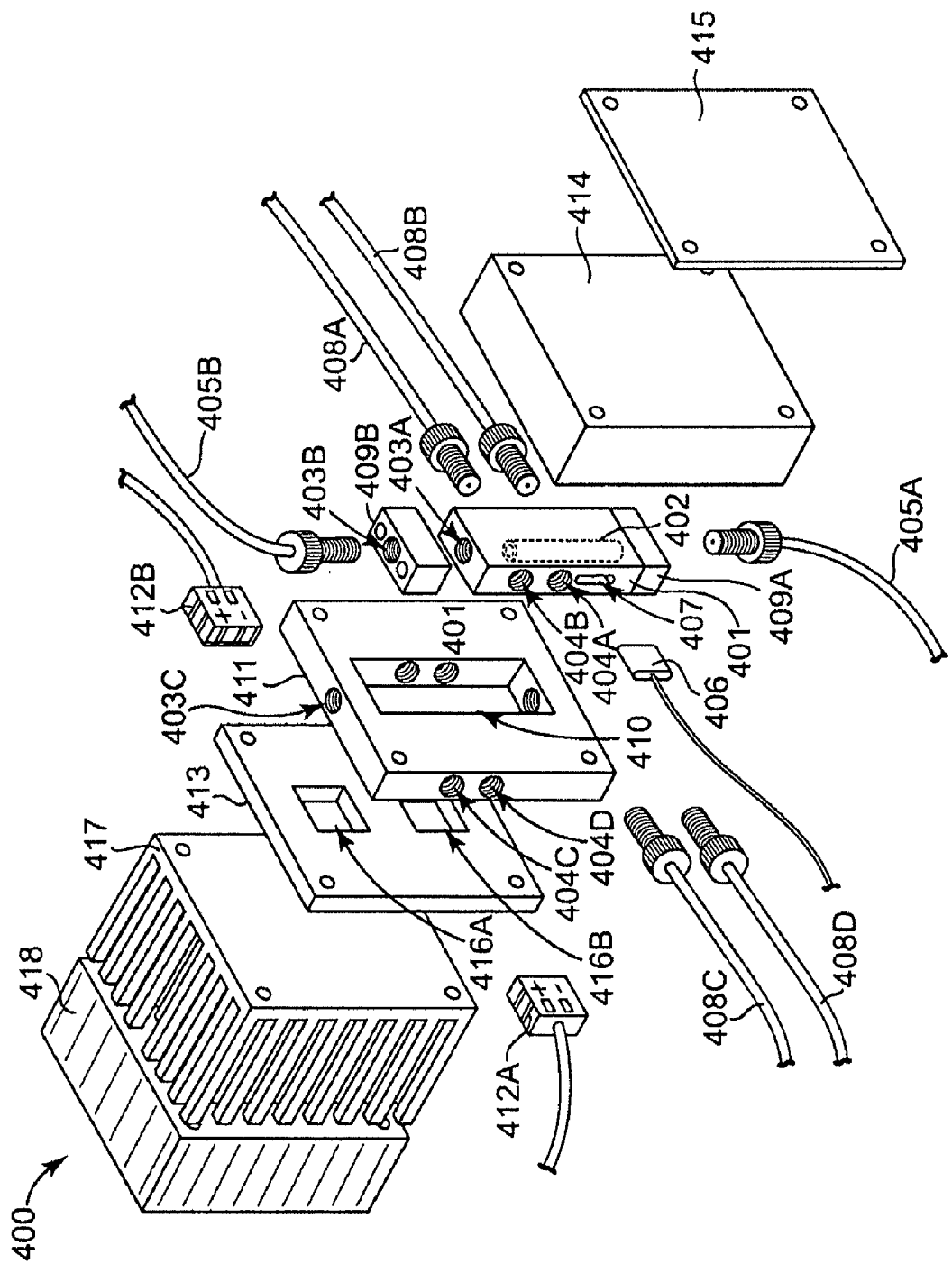
FIG. 6 is a schematic diagram illustrating an exploded view of a temperature regulated flow optical sensor.

FIG. 6 is a schematic diagram illustrating an exploded view of a temperature regulated optical sensor 400. Optical sensor 400 is one example of an optical sensor which may be used as the detector 222 of FIG. 1. As mentioned above, however, it shall be understood that other optical sensors/detectors may also be used without departing form the scope of the present invention. Furthermore, other detectors such as pH, ORP, conductivity or other sensors may be used within the scope of the invention.

At the core of optical sensor 400 is a cell holder 401 which in use contains an optical cell 402 into which the sample of the use composition, the reagent(s) and the carrier are drawn and in which the calorimetric detection is performed. In this embodiment, optical cell 402 is made of glass. However, optical cell 402 may also be made of any other appropriate material through which optical calorimetric analysis may be performed, such as quartz, sapphire, optical ceramic and other examples known to those of skill in the art.

The sample is brought into optical sensor 400 from static mixer 220 (FIG. 1) via input tubing 405A and exits optical sensor 400 via output tubing 405B. Two sets of optical fibers, input fibers 408A and 408B and corresponding output fibers 408C and 408D, allow optical sensor to perform optical analysis of the sample using multiple wavelengths. For example, response data may be obtained using two wavelengths, which may result in a more flexible and/or robust system. Wavelength selection is based on spectral response of the triiodide complex, and may be within the range of 350 to 450 nanometers, for example. In one embodiment, a two wavelength system may utilize the wavelengths 375 nanometers and 405 nanometers, for example.

Cell holder 401 has a channel 403 through which optical cell 402 is inserted and resides after assembly of optical sensor 400. Cell holder 401 also has first and second optical input ports 404A and 404B for connection of input optical fibers 408A and 408B. Cell holder also includes first and second optical output ports 404C and 404D (not shown in FIG. 6) for connection of output optical fibers 408C and 408D. In this embodiment, cell holder 401 also includes an input cover 409A and an output cover 409B, each having a bore 403B corresponding to central bore 403A of cell holder 401.

Optical sensor 400 is temperature regulated. Namely, optical sensor 400 regulates the temperature within cell holder 401 so as to maintain a relatively cool temperature (compared to room temperature) at which optical analysis of the use composition sample takes place. Analysis of the use composition sample at low temperature is done for several reasons. Rates of chemical reactions are temperature dependent. Control of the temperature at which the kinetic measurements are made precludes the need for temperature lookup tables. In addition, the rates of chemical reactions increase with increasing temperature. As the reaction between iodide and hydrogen peroxide is slower than the reaction between peracid and iodide this effect may be enhanced at lower temperatures. Although lower temperatures are by no means required for the present invention, subambient temperatures may enhance the difference in reaction rates. Thus, in some embodiments, the measurements may be taken with the sample mixture at ambient temperatures (generally between about 20° C. and 25° C.). In other embodiments, subambient temperatures (e.g., less than 25° C.) may be used. Depending upon the temperature of the location where the measurements are to take place, the sample mixture may be cooled to temperatures approaching the freezing temperature of water (for example, as low as about 5° C.). In general, the temperature at which measurements are taken may be in the range of 5 to 25° C., or more narrowly between 10 and 18° C.

To measure the temperature of the sample mixture, optical sensor 400 includes a temperature sensor 406 placed within a slot 407 of cell holder 401. Temperature sensor 406 is positioned within slot 407 so as to sense the temperature at or very near the surface of optical cell 402, resulting in a relatively accurate reading of the temperature of the use composition sample contained within optical cell 402. A first insulation plate 411 includes a cut out 410 substantially sized to receive cell holder 401, first and second input ports 404C and 404D corresponding to first and second input ports 404A and 404B of cell holder 401, and a channel 403C corresponding to channel 403A of cell holder 401.

At least one thermoelectric module 412 (two in this example, thermoelectric modules 412A and 412B) control the internal temperature of optical sensor 400 so as to maintain the cooled temperature of the sample mixture. In this embodiment, thermoelectric modules 412A and 412B are fitted within corresponding cutouts 416A and 416B of a second insulation plate 413. A third insulation plate 414 provides for further insulation of the optical cell 402. A support plate 415 provides an outer wall for optical sensor 400.

Heat sink 417 and fan 418 draw heat away from cell holder 401 to so as to maintain a relatively constant internal temperature at or near optical cell 402 where optical analysis of the sample of the use composition takes place. A third insulation plate 414 provides for further insulation of the optical cell 402. A support plate 415 provides an outer wall for optical sensor 400.

In the embodiment of FIGS. 6A-6D, the sample of the use composition, the reagent and the carrier are mixed in static mixer 222 as shown in FIG. 1. As discussed above the peracid concentration is proportional to the adjusted y-intercept, $b_{adj}$, where $b_{adj}$ is extrapolated back from the time that the sample mixture arrives in the detector (time $t_0$) to the time that the reaction takes place (time $t_0 - t_{lag}$) using the known linear relationship between absorbance and time for the sample mixture.

In another embodiment, optical sensor 400 includes an internal mixer located within optical cell 402 to reduce the time $t_{lag}$ between when the sample mixture arrives in the detector (time $t_0$) to the time that the reaction takes place (time $t_0$-$t_{lag}$). One example of such an embodiment is shown in FIGS. 7A and 7B.

Figure 7A:
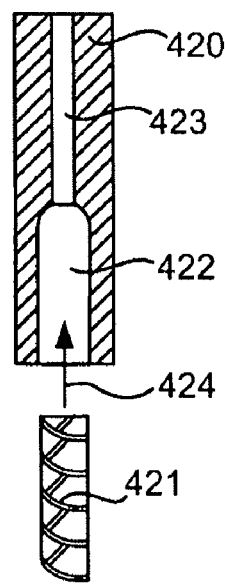
FIG. 7A illustrates a glass cell with an internal mixer.
Figure 7B:
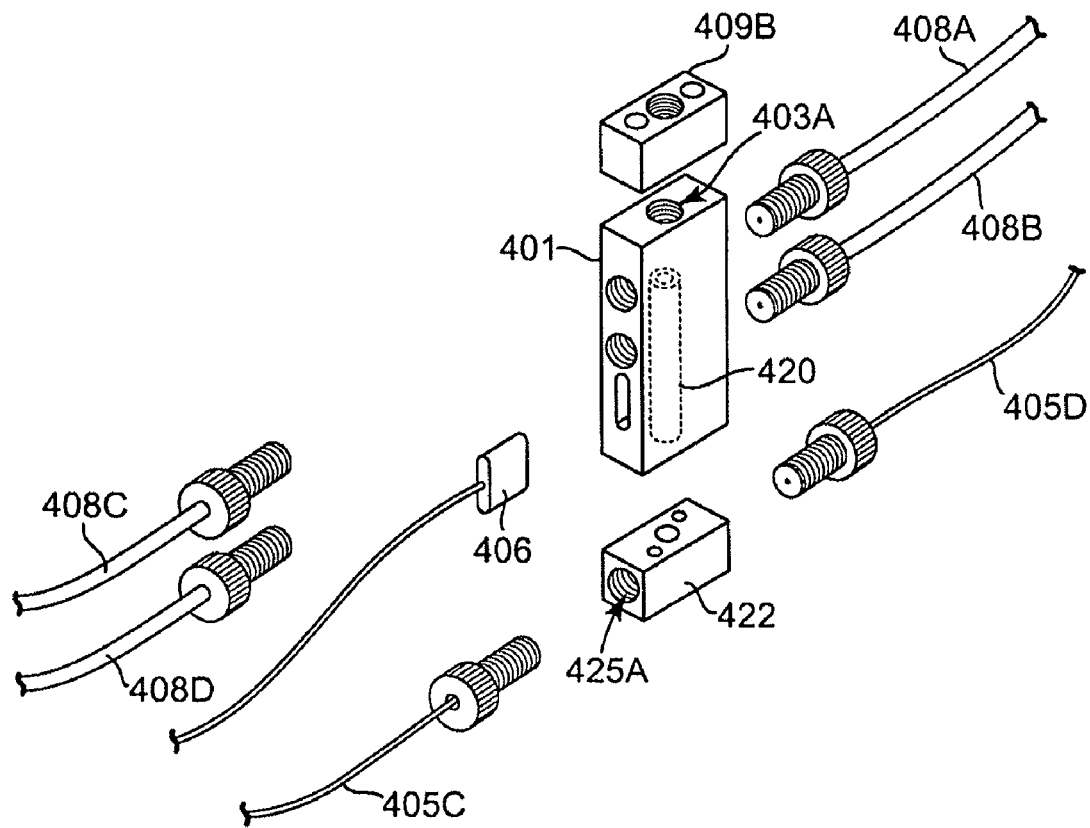
FIG. 7B is a schematic diagram illustrating an exploded view of a temperature regulated flow cell with two input ports and a glass cell having an internal mixer.

FIG. 7A illustrates an optical cell 420 with an internal mixer 421, and FIG. 7B is a schematic diagram illustrating an exploded view of an optical sensor 430 having two input ports incorporating the optical cell 420 with internal mixer 421 of FIG. 7A. In order to decrease the time between which the diluted use solution and the reagent(s) are mixed and the resulting sample mixture is introduced into the optical cell for analysis, optical cell 420 is fabricated to include a mixer cavity 422 sized to receive a static mixer 421. Static mixer is inserted into mixer cavity 422 in the direction indicated by arrow 424. Optical cell 420 also includes an analysis channel 423 in which the sample mixture is analyzed. In this embodiment optical cell 420 is made of glass but may also be made of any other material appropriate for conducting optical analysis, such as quartz, sapphire or optical ceramic.

To accommodate optical cell 420 with internal mixer 421, the embodiment shown in FIG. 1 is modified so as not to include static mixer 220. Instead, the diluted use solution and the reagent(s) are simultaneously dispensed directly into detector 222, which in this case would be implemented using an embodiment of an optical sensor 430 such as that shown in FIG. 7B.

The diluted use solution and the reagent(s) are simultaneously dispensed directly into optical sensor 430 via use solution input tubing 405C and reagent solution input tubing 405D. Cover 422 is modified from cover 309A in FIG. 6 to include two input ports 425A and 425B (425B not visible in FIG. 7B). The diluted use solution and the reagent(s) are thus simultaneously dispensed directly into static mixer 421. As the diluted use solution and the reagent(s) are dispensed through static mixer 421 and into analysis channel 423, they are mixed and begin to react. By incorporating the mixer to be immediately adjacent analysis channel 423 of the optical cell, the time lag $t_{lag}$ may be reduced, resulting in a more accurate determination of the peracid concentration in the use solution.

Figure 8:
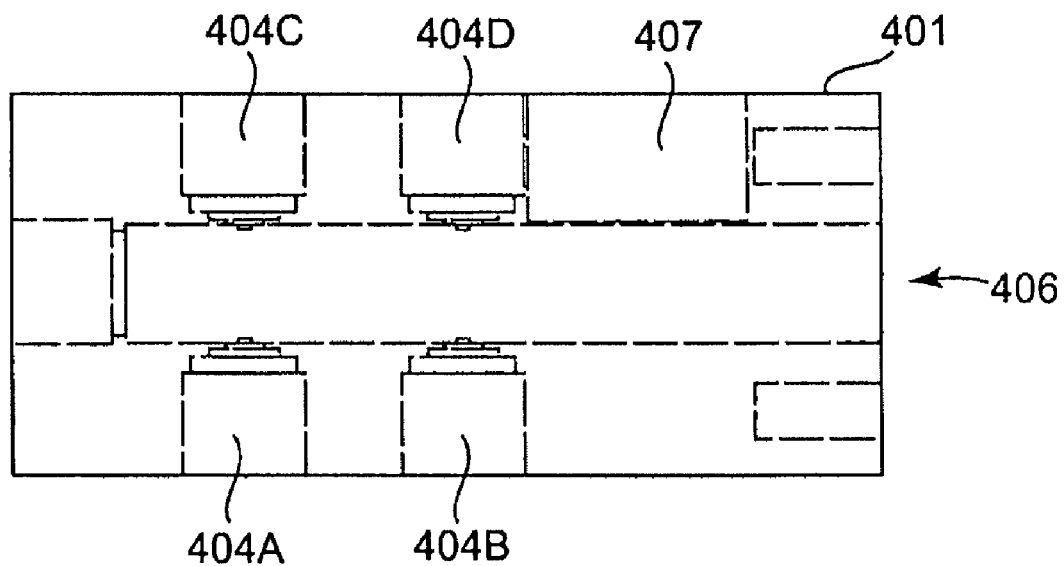
FIG. 8 is a schematic illustrating a cross-sectional right side view of an optical cell holder having a single input port.

FIG. 8 illustrates a front cross sectional view of the example cell holder 401 shown in FIGS. 6 and 7B. As discussed above, cell holder 401 includes a channel 406 into which the optical cell is received, slot 407 into which temperature sensor 406 is received, first and second optical input ports 404A and 404B and first and second optical output ports 404C and 404D. The diameter of channel 406 is determined based at least in part on the desired sensitivity of the measurements to be taken. For example, channel 406 may have a diameter of approximately 6 mm and the internal channel of optical cell may have a diameter from approximately 1 mm to approximately 3 mm.

Figure 9:
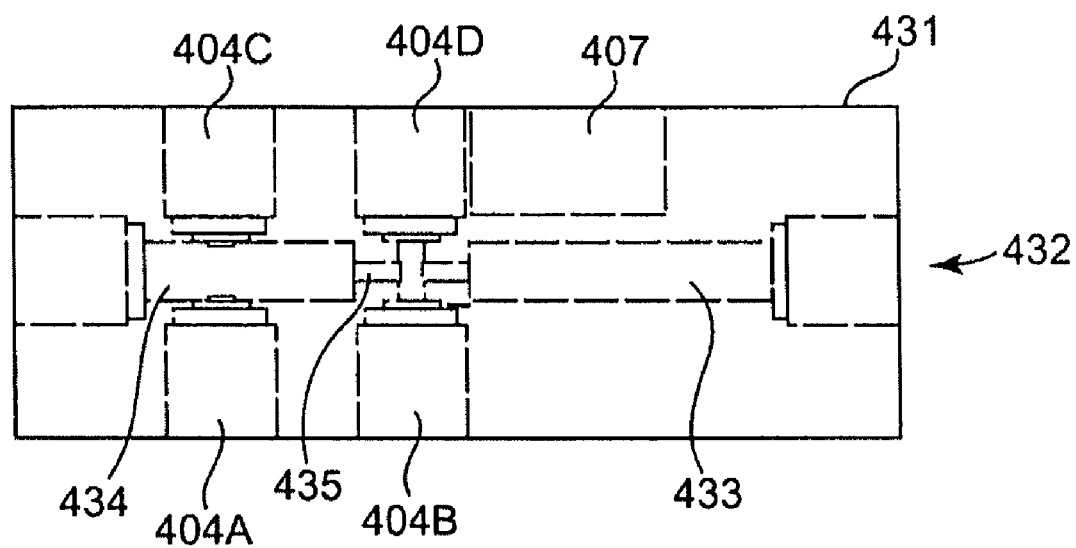
FIG. 9 is a schematic illustrating a cross-sectional right side view of an optical cell holder having two input ports.

FIG. 9 illustrates a front cross sectional view of another embodiment of a cell holder 430. In this embodiment, cell holder 430 is designed to receive the sample mixture directly without requiring insertion of a separate optical cell. In this embodiment, cell holder 430 may be fabricated from any suitable material, such as stainless steel, for example, passivated stainless steel 316, or optical ceramic. Cell holder 430 includes a channel 432, slot 407 into which temperature sensor 406 is received, first and second optical input ports 404A and 404B and first and second optical output ports 404C and 404D. The inner part of channel 432 of cell holder 430 further includes multiple subchannels each having a different diameter. The mixer subchannel 433 is sized to receive a static mixer in a manner similar to that described above with respect to FIGS. 6, 7A and 7B. First analysis subchannel 434 is positioned in the optical path created by first optical input port 404B and first optical output port 404D. Second analysis subchannel 435 is positioned in the optical path created by second optical input port 404B and second optical output port 404D. The differing diameters of first and second analysis subchannels 434 and 435 provide for differing sensitivity in absorbance measurement. For example, in one embodiment, subchannel 434 may have a diameter of 3 mm and subchannel 435 may have a diameter of 1 mm, for example.

Figure 19:
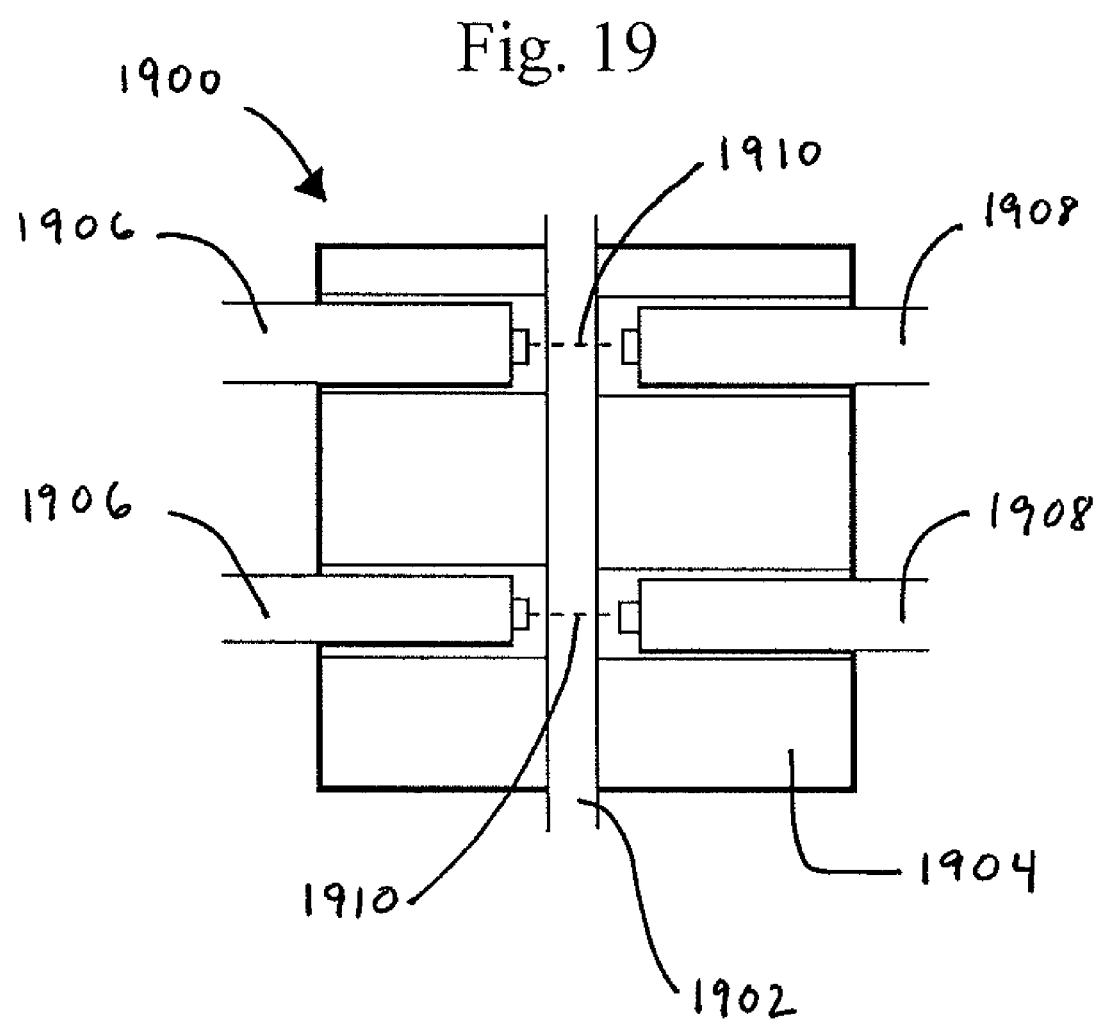
FIG. 19 is a schematic of a reduced turbulence optical cell having according to some embodiments.

FIG. 19 shows a modified cell design for obtaining appropriate response data according to some embodiments of the invention. One problem with many detector line arrangements is turbulence. Turbulence can be caused by numerous conditions within the analysis system. Disturbances in sample flow can occur at tubing-device interfaces due to variations in the tolerance of the coupling. In addition, variations of the inner diameter of the tubing can produce vortexes which change the mixing efficiency and uniformity of the reaction mixture inside of the detector line. A further source of sample turbulence is the mechanism of sample mixing. Some mixers operate by subjecting the reactants to turbulence, for example, static mixers or a T-junction mixers. If the turbulence induced to mix the sample by such mixers is present when the sample reaches the optical cell, measurement repeatability can be negatively impacted. Finally, reactions involving reagents, carriers, and use compositions having different specific gravities can exhibit regions of variable mixing, enhancing the effect of turbulence within an optical detection system.

Figure 20:
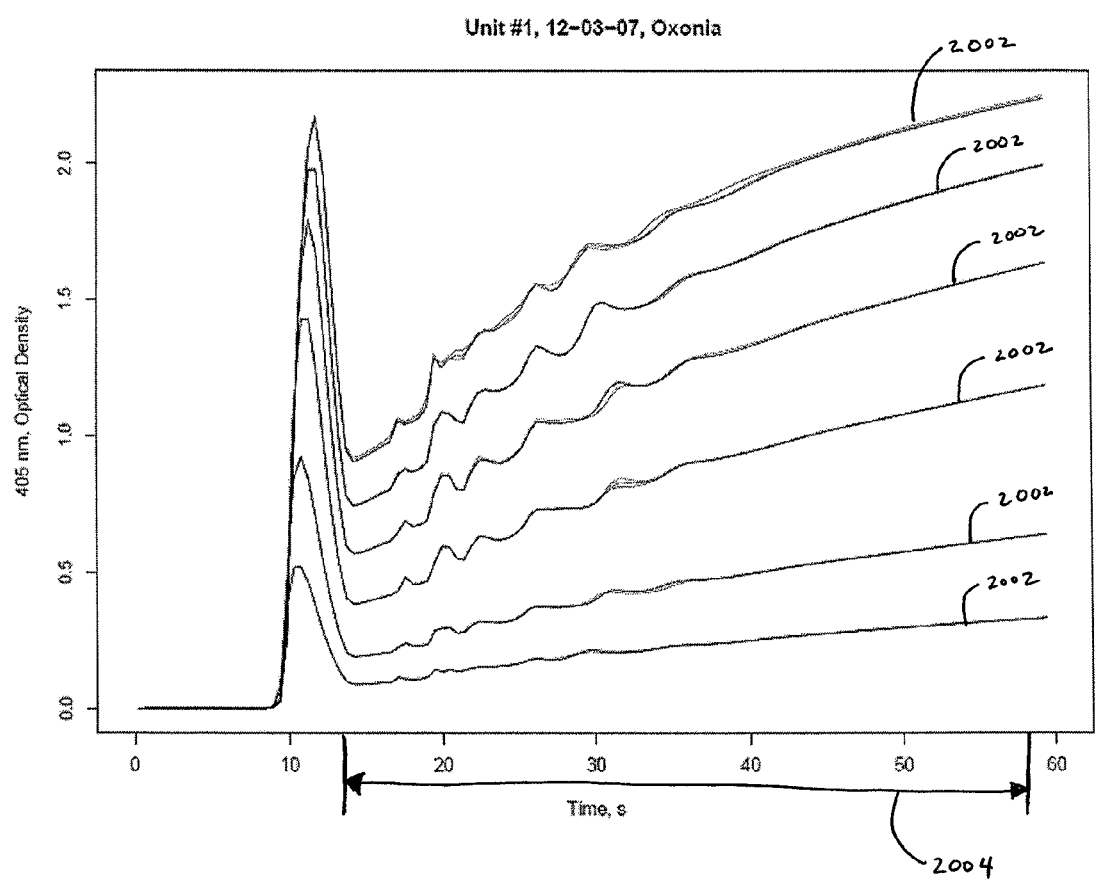
FIG. 20 is a plot of optical density versus time for a plurality of sample solutions illustrating response data subject to turbulence.
Figure 21:
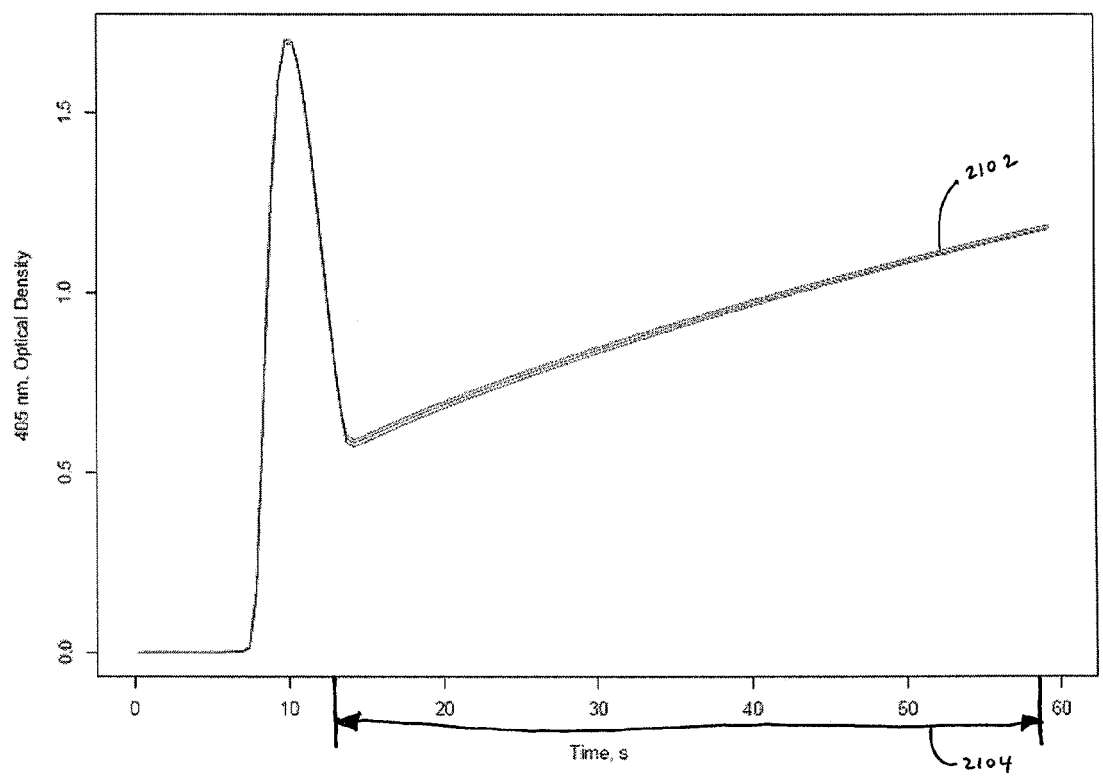
FIG. 21 is a plot of optical density versus time for a plurality of sample solutions illustrating appropriate response data according to some embodiments.

FIGS. 20 and 21 illustrate examples of the effect of turbulence on response data collected from systems according to embodiments of the invention. FIG. 20 shows response data from a system such as those described above. FIG. 21 shows response data from an analysis system that is substantially turbulence free according to some embodiments. The response data 2002 of FIG. 20 shows significant oscillations and disturbances during the measurement period 2004 (i.e. the period where the measurement locations along the measurement profile is stopped within the cell). These oscillations can introduce error into the regression analysis leading to less accurate results. Further, oscillations can introduce random error into measurement procedures significantly reducing repeatability. In contrast, the response data 2102 of FIG. 21 is generally oscillation free during the measurement period 2104. According to some preferred embodiments of the invention, FIG. 21 is representative of "appropriate response data." More generally, the methods and devices for turbulence reduction described herein can be particularly beneficial for optical analysis of kinetic chemistries. This is especially true of kinetic assay procedures using stopped flow analysis.

In some embodiments, improvements in accuracy and repeatability of measurement data can be achieved by the use of laminar flow mixing in combination with a detector line and an optical cell designed for reduced-turbulence. In one such system, the turbulence reduction system comprises a single length of tubing from the multiport valve to the drain. The tubing is fluidly connected to the multiport valve, passes through the optical cell, and connects to or empties into the drain. In some embodiments, laminar flow mixing is introduced along the tubing between the multi-port valve and the optical cell. Laminar flow mixing can be accomplished by, for example, coiling a length of the tubing. In some embodiments, the laminar flow mixing coil can comprise a coil having a diameter of approximately 3 inches. No intermediate connection points or junctions are positioned along the tubing, thus avoiding sample disturbance caused by variations in the tolerance of the coupling. Moreover, the tubing should be free of sharp turns or kinks as such features can introduce turbulence to the sample.

Referring back to FIG. 19, the optical cell 1900 shown can reduce sample turbulence by allowing for the use of a single tubing 1902 having a substantially constant diameter along the entire length of the detector line (i.e. from multiport valve 218 to waste line 224 of FIG. 1). In this embodiment, the optical cell 1900 comprises a cell body 1904 positioned about the detector line tubing 1902. In some embodiments, the optical cell is designed to allow the tubing 1902 to pass through the cell body 1904 in a substantially straight path. Cell designs seeking to increase the optical path length by providing sharp turns or bends within the detector line (e.g. a Z-cell) should generally not be used. Such sharp turns or bends within the detector line can cause turbulence of the sample as described above.

The optical cell 1900 of FIG. 19 further includes two emitters 1906 and two detectors 1908 positioned within the cell body 1904 about a transparent portion of the tubing 1902. Each detector 1908 is positioned opposite an emitter 1906 such that the detector can receive light directed along an optical path 1910 by the emitter. The optical paths 1910 traverse the transparent portion of the detector line tubing 1902 and therefore pass through sample contained therein. In some embodiments, the emitter comprises a wave guide (e.g. a fiber optic element) connected to a light source (e.g. a laser or light emitting diode) which is isolated from the optical cell body. By contrast, in some embodiments, the emitter comprises a light source directly installed within the cell body. Likewise, the detector can comprise a wave guide connected to an optical detector isolated from the optical cell body or can be directly installed within the cell body. In some embodiments, the transparent portion of the tubing 1902 comprises but a portion of an otherwise opaque tube. Alternatively, in some embodiments, the entire length of the tubing 1902 is transparent, the tube comprising a polymer, e.g. a fluoropolymer such as, for example, polytetrafluoroethylene, i.e. Teflon.

Figure 22A:
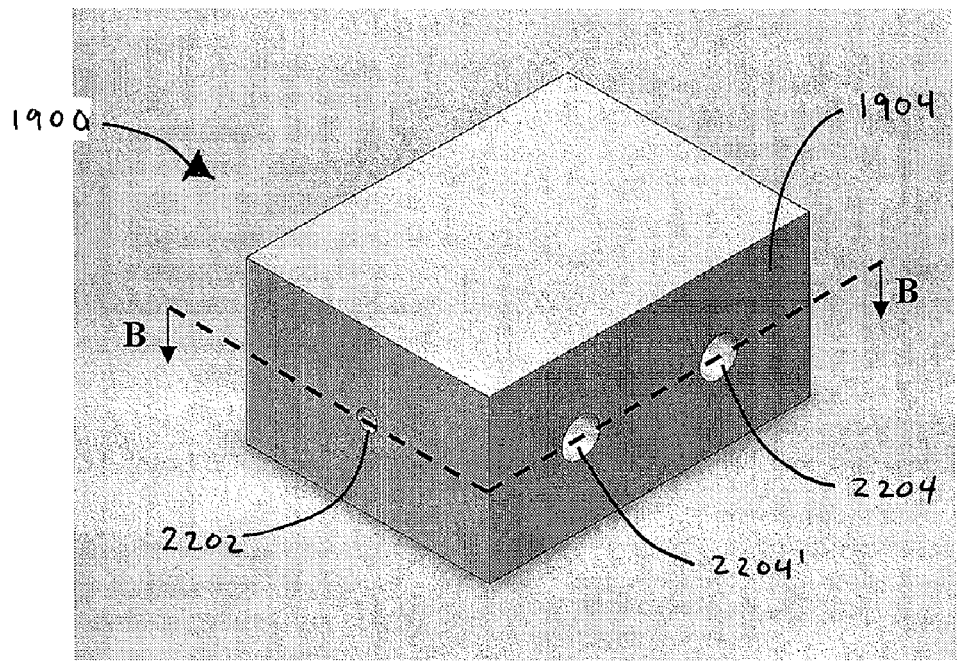
FIG. 22A is a perspective view of a cell body according to some embodiments.
Figure 22B:
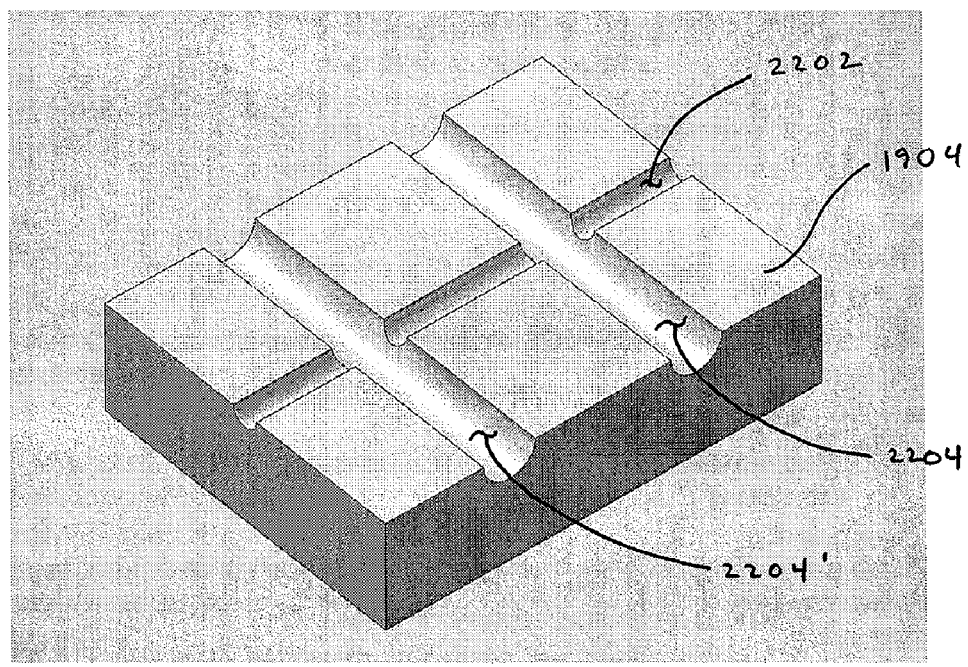
FIG. 22B is a perspective view of a section of the cell body of FIG. 22A taken along line B-B.

FIGS. 22A and 22B show additional views of a cell body 1904, such as that of FIG. 19. The cell body 1904 includes a first pathway 2202 to receive the detector line tubing. A second pathway 2204 passes the cell body 1904 and intersects the first pathway 2202 therewithin. The second pathway 2204 is adapted to receive an emitter/detector pair such as those shown in FIG. 19. The shown embodiment further includes an additional pathway 2204' intersecting the first pathway 2202 for receiving an additional emitter/detector pair. The second and additional pathways 2204, 2204' are oriented generally perpendicular to the first pathway 2202. While embodiments of the cell body have been shown to include two detector/emitter pairs, one should recognize that cell bodies according to embodiments of the invention can include one or more than two detector/emitter pairs. Moreover, it should be recognized that the turbulence reduction systems and optical cell designs described above can be used with other sample preparation systems.

Some embodiments of peracid/peroxide monitors can further be optimized for use as an on site monitor. That is, there is a need for accurate and reliable sensors to measure peracid and peroxide concentrations when ambient temperature can vary in wide range. Unstable temperature inside of a system have been found to contribute to random variations in concentration readings. More particularly, the absorbance of the above-described analytical solutions used in flow injection can experience changes in absorbance if temperatures of sample and reagent are not repeatable and not stable. Potential causes of such temperature instability include environmental temperature variances and locally generated heat and air flow from components of the measurement system such as pumps, step motors, and controllers within the monitor. Thus, some embodiments include additional features to isolate the sample from potential heat sources at all stages of operation and to facilitate use of monitors and methods according in various operating environments. In addition, systems according to some embodiments provide means for adjusting or stabilizing the temperature of sample prior to delivery to the detector to avoid the inconsistencies associated with in field operation.

Figure 23:
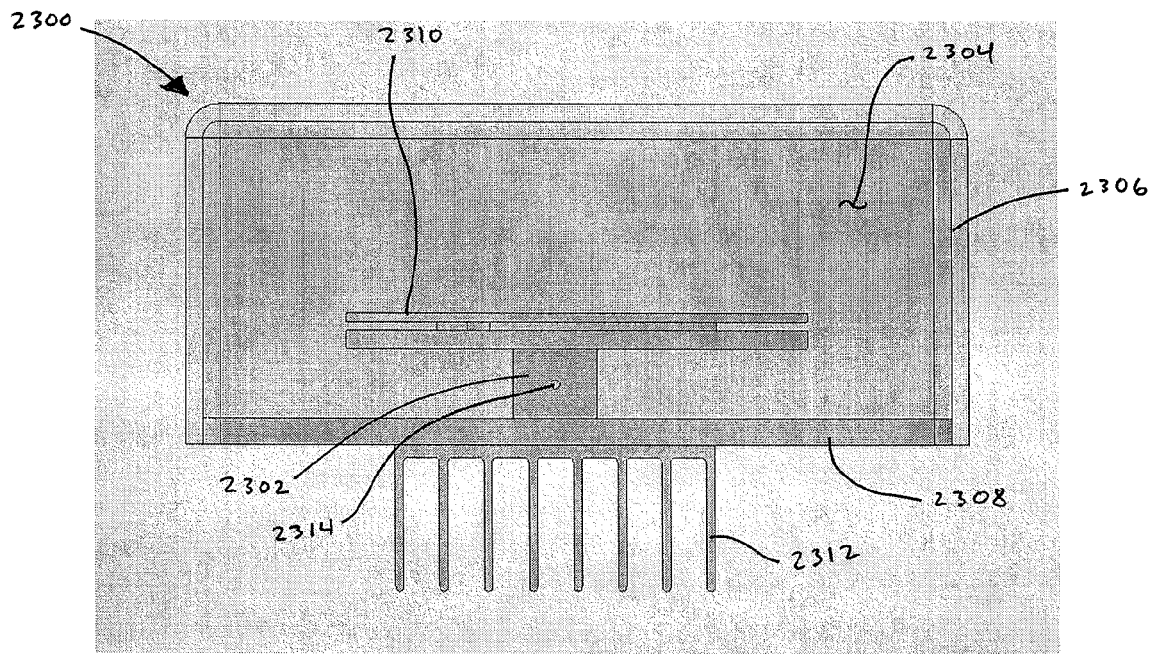
FIG. 23 is a front plan view of a temperature stabilized optical cell and sample preparation area according to some embodiments.
Figure 24:
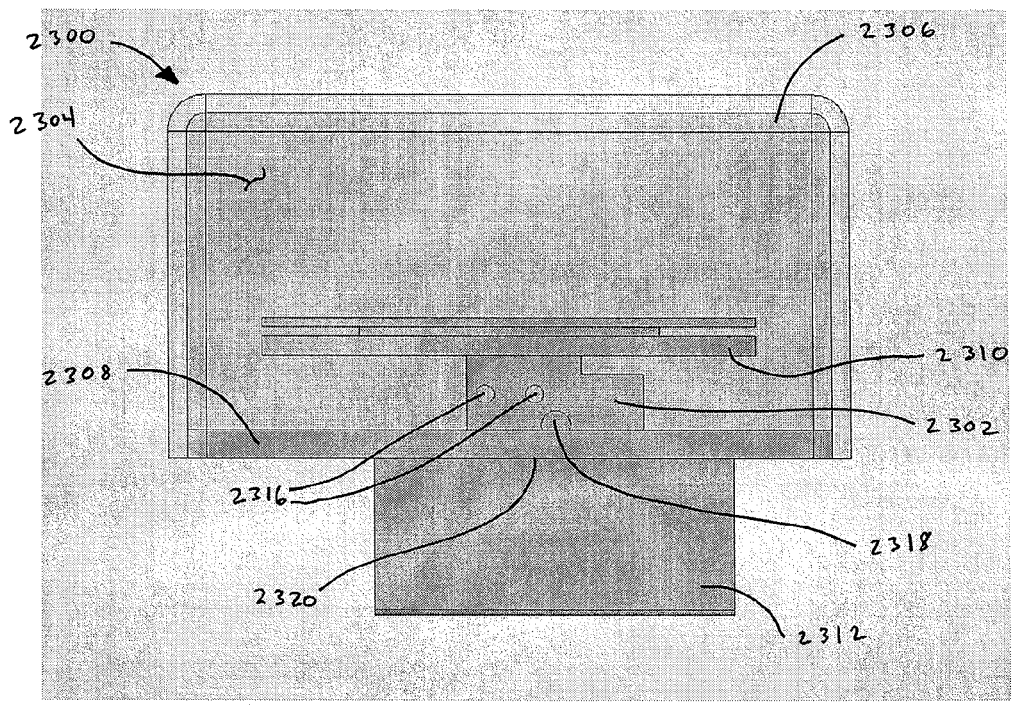
FIG. 24 is a side plan view of the temperature stabilized optical cell and sample preparation area of FIG. 23.
Figure 25:
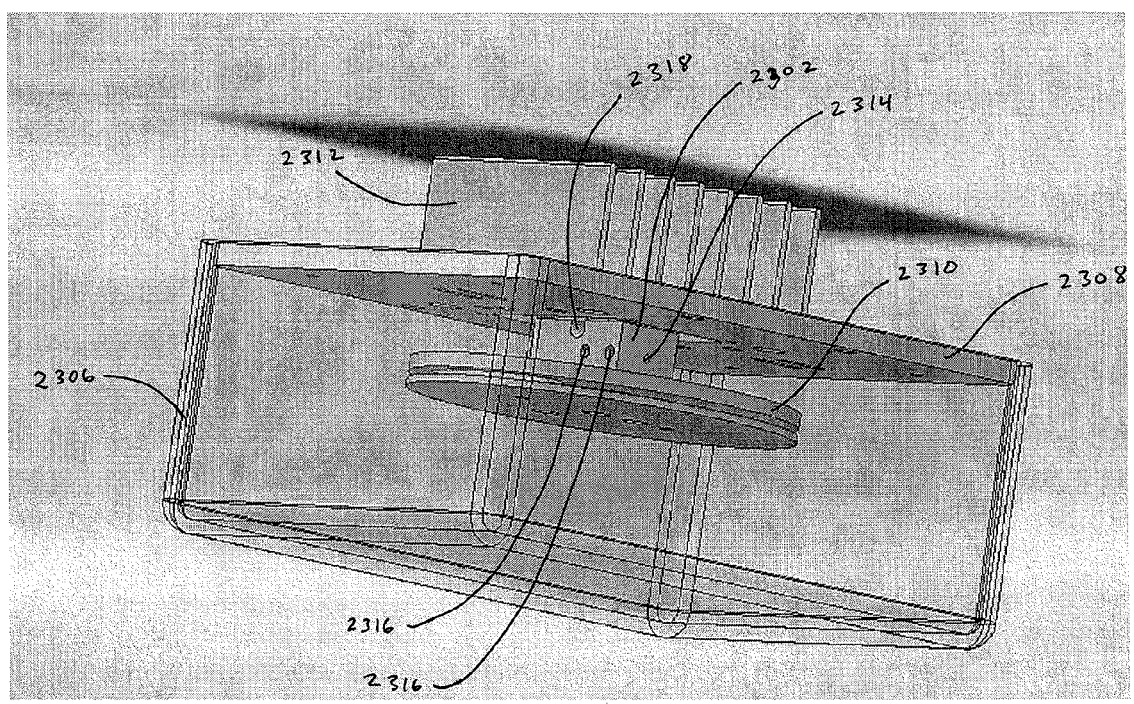
FIG. 25 is a perspective view of the temperature stabilized optical cell and sample preparation area of FIG. 23.

An embodiment of an optical sensor and sample preparation area (mixing coil) optimized for use as an on site monitor is shown in FIGS. 23-25. The temperature-regulated optical sensor 2300 generally comprises a cell housing 2302 installed within an insulated cavity 2304 of an insulating enclosure 2306. The cell housing 2302 comprises a thermally conductive material and can be generally of the form of the above described cell housings. A sample line can enter the insulated cavity through an entry port in a mounting plate 2308 or wall of the enclosure. Once within the insulated cavity 2304, the sample line can be coiled about a spool 2310 contained therein to provide a non turbulent mixing coil. The spool 2310 can be mounted to the cell housing 2302 and likewise comprise a thermally conductive material. In this manner, the spool 2310 can draw heat from or deliver heat to sample within the sample line as it passes through the mixing coil. Heat can then pass through the thermally conductive cell housing 2302 and out of the system 2300 via a connected heat sink 2312. The sample line then passes through bore 2314 within the cell housing 2302 where emitter/detectors installed in emitter detector pathways 2316 can be used to analyze the sample. The sample line can then deliver the sample out of the optical cell 2302 via an exit port within the mounting plate 2308 or enclosure wall.

Further, embodiments of the improved optical sensor can include a thermoelectric heat transfer element (not shown) installed within an opening in the mounting plate 2308 and between the cell housing 2302 and an exterior surface 2320 of the enclosure 2306. Heat sink 2312 can be coupled with the thermoelectric heat transfer element. The thermoelectric heat transfer element can comprise any such device capable of effectuating heat transfer (uni- or bi-directional) under the application of an electrical current or voltage. In a preferred embodiment, the thermoelectric heat transfer element comprises a Peltier device, however, other devices are envisaged. Still further, some embodiments can include a fan (not shown) coupled to the device so as to direct air about the heat sink 2312 to further facilitate heat transfer from the device.

Embodiments of the optical cell can be controlled by a controller. In some embodiments, the controller is processor 212 of FIG. 1. The controller can regulate the thermoelectric heat transfer element and fan to control the temperature of the cell. A temperature sensor 2318 can be coupled with the cell housing or elsewhere within the cell to provide feedback to the controller for temperature regulation purposes. In some preferred embodiments, the temperature of the cell and sample preparation area (coil) is controlled to be approximately 24 degrees Celsius. In such case, embodiments can provide for stable operation within environmental temperatures ranging from approximately 10 degrees Celsius to approximately 30 degrees Celsius (e.g. 15 degrees C. to 28 degrees C.). In some cases, system stability can be improved by a factor of two to three. For example, deviations were not more than 7% for POA from concentrations of 1750 ppm to 2500 ppm and hydrogen peroxide from 5000 ppm to 40,000 ppm.

The compositions described herein may be used for a variety of domestic or industrial applications, e.g., to reduce microbial or viral populations on a surface or object or in a body or stream of water. The compositions may be applied in a variety of areas including kitchens, bathrooms, factories, hospitals, dental offices and food plants, and may be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces may be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces may be made from a variety of materials including, for example, paper, fiber, woven or nonwoven fabric, soft plastics and elastomers. The compositions may also be applied to soft surfaces such as food and skin (e.g., a hand). The use compositions may be employed as a foaming or nonfoaming environmental sanitizer or disinfectant.

The compositions may be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The compositions may also be used in veterinary products such as mammalian skin treatments or in products for sanitizing or disinfecting animal enclosures, pens, watering stations, and veterinary treatment areas such as inspection tables and operation rooms. The compositions may be employed in an antimicrobial foot bath for livestock or people.

The compositions may be employed for reducing the population of pathogenic microorganisms, such as pathogens of humans, animals, and the like. The compositions may exhibit activity against pathogens including fungi, molds, bacteria, spores, and viruses, for example, *S. aureus, E. coli*, Streptococci, *Legionella, Pseudomonas aeruginosa*, mycobacteria, tuberculosis, phages, or the like. Such pathogens may cause a varieties of diseases and disorders, including Mastitis or other mammalian milking diseases, tuberculosis, and the like. The compositions may reduce the population of microorganisms on skin or other external or mucosal surfaces of an animal. In addition, the compositions may kill pathogenic microorganisms that spread through transfer by water, air, or a surface substrate. The composition need only be applied to the skin, other external or mucosal surfaces of an animal water, air, or surface.

The compositions may also be used on foods and plant species to reduce surface microbial populations; used at manufacturing or processing sites handling such foods and plant species; or used to treat process waters around such sites. For example, the compositions may be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions may be used to treat produce transport waters such as those found in flumes, pipe transports, cutters, slicers, blanchers, retort systems, washers, and the like. Particular foodstuffs that may be treated with compositions include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The composition may be useful in the cleaning or sanitizing of containers, processing facilities, or equipment in the food service or food processing industries. The compositions may be used on food packaging materials and equipment, including for cold or hot aseptic packaging. Examples of process facilities in which the compositions may be employed include a milk line dairy, a continuous brewing system, food processing lines such as pumpable food systems and beverage lines, etc. Food service wares may be disinfected with the compositions. For example, the compositions may also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The compositions may also be used on or in other industrial equipment and in other industrial process streams such as heaters, cooling towers, boilers, retort waters, rinse waters, aseptic packaging wash waters, and the like. The compositions may be used to treat microbes and odors in recreational waters such as in pools, spas, recreational flumes and water slides, fountains, and the like.

A filter containing a composition may reduce the population of microorganisms in air and liquids. Such a filter may remove water and air-born pathogens such as *Legionella*.

The compositions may be employed for reducing the population of microbes, fruit flies, or other insect larva on a drain or other surface.

The compositions may also be employed by dipping food processing equipment into the use solution, soaking the equipment for a time sufficient to sanitize the equipment, and wiping or draining excess solution off the equipment. The compositions may be further employed by spraying or wiping food processing surfaces with the use solution, keeping the surfaces wet for a time sufficient to sanitize the surfaces, and removing excess solution by wiping, draining vertically, vacuuming, etc.

The compositions may also be used in a method of sanitizing hard surfaces such as institutional type equipment, utensils, dishes, health care equipment or tools, and other hard surfaces. The composition may also be employed in sanitizing clothing items or fabrics which have become contaminated. The composition is contacted with any contaminated surfaces or items at use temperatures in the range of about 4° C. to 60° C., for a period of time effective to sanitize, disinfect, or sterilize the surface or item. For example, the composition may be injected into the wash or rinse water of a laundry machine and contacted with contaminated fabric for a time sufficient to sanitize the fabric. Excess composition may be removed by rinsing or centrifuging the fabric.

The compositions may be applied to microbes or to soiled or cleaned surfaces using a variety of methods. These methods may operate on an object, surface, in a body or stream of water or a gas, or the like, by contacting the object, surface, body, or stream with a composition. Contacting may include any of numerous methods for applying a composition, such as spraying the composition, immersing the object in the composition, foam or gel treating the object with the composition, or a combination thereof.

The composition may be employed for bleaching pulp. The compositions may be employed for waste treatment. Such a composition may include added bleaching agent.

Other hard surface cleaning applications for the compositions include clean-in-place systems (CIP), clean-out-of-place systems (COP), washer-decontaminators, sterilizers, textile laundry machines, ultra and nano-filtration systems and indoor air filters. COP systems may include readily accessible systems including wash tanks, soaking vessels, mop buckets, holding tanks, scrub sinks, vehicle parts washers, non-continuous batch washers and systems, and the like.

Although specific embodiments of a dispenser system have been shown and described, it shall be understood that other embodiments could be substituted therefore without departing from the scope of the present invention. Various embodiments of the invention have been described. These and other embodiments are within the scope of the following claims.

What is claimed is:

1. A method comprising:
    mixing a sample of a use composition with at least one reagent, the use composition comprising a concentration of a peracid and a concentration of a peroxide;
    delivering the sample mixture to an optical cell;
    selecting a wavelength for analyzing the sample mixture based on at least one of an estimated concentration of the peracid or an estimated concentration of the peroxide, wherein the wavelength is selected from at least a first wavelength associated with a first estimated concentration of the peracid or a first estimated concentration of the peroxide, and a second wavelength associated with a second estimated concentration of the peracid or a second estimated concentration of the peroxide, wherein the second wavelength is greater than the first wavelength, the second estimated concentration of the peracid is greater than the first estimated concentration of the peracid, and the second estimated concentration of peroxide is greater than the first estimated concentration of peroxide;
    measuring an optical response of the sample mixture in the optical cell at the selected wavelength, thereby obtaining response data indicative of absorbance of the sample mixture as a function of time; and
    determining the concentration of the peracid and the concentration of the peroxide in the use composition based on the response data wherein the first estimated peracid concentration is between 100 parts per million (ppm) and 1000 ppm and the first estimated peroxide concentration is between 100 ppm and 5000 ppm, or the second estimated peracid concentration is between 1000 ppm and 5000 ppm and the second estimated peroxide concentration is between 5000 ppm and 40,000 ppm.

2. The method of claim 1, wherein the second estimated peracid concentration is between 1000 parts per million (ppm) and 5000 ppm, and the second estimated peroxide concentration is between 5000 ppm and 40,000 ppm.

3. The method of claim 2, wherein the first estimated peracid concentration is between 100 ppm and 1000 ppm, and the first estimated peroxide concentration is between 100 ppm and 5000 ppm.

4. The method of claim 1, wherein the second estimated peracid concentration is between 1000 ppm and 5000 ppm.

5. The method of claim 1, wherein mixing the sample of the use composition with at least one reagent further comprises mixing the sample of the use composition with a diluent comprising water.

6. The method of claim 1, wherein the at least one reagent includes an iodide solution with a pH adjusted to an alkaline range.

7. The method of claim 1, wherein the at least one reagent includes potassium iodide.

8. The method of claim 1, wherein mixing the sample of the use composition with at least one reagent further comprises mixing the sample with a dilute acid.

9. The method of claim 8, wherein the dilute acid includes acetic acid.

10. The method of claim 1, wherein mixing the sample comprises:
    loading a volume of the use composition within a sample line connected to the optical cell;
    then loading a volume of diluent within the sample line;
    then loading a volume of an acid within the sample line; and
    then loading a volume of reagent within the sample line.

11. The method of claim 1, wherein when the estimated peracid concentration is between 1000 ppm and to 5000 ppm, mixing the sample comprises:
    loading from 50 microliters to 200 microliters of the use composition within a sample line connected to the optical cell;
    then loading 50 microliters to 500 microliters of a diluent within the sample line;
    then loading 50 microliters to 200 microliters of acetic acid within the sample line; and
    then loading 50 microliters to 200 microliters of potassium iodide within the sample line.

12. The method of claim 1, wherein mixing the sample comprises:
    loading the use composition into a sample line connected to the optical cell;
    loading the at least one reagent reagents and a barrier within a separate holding line; and
    coupling the separate holding line with the sample line to load the barrier and the at least one reagent into the sample line.

13. The method of claim 1, wherein mixing the sample comprises providing for laminar mixing of the sample.

14. The method of claim 13, wherein the laminar mixing is provided by delivering the sample through a mixing coil.

15. The method of claim 1, wherein delivering the sample to the optical cell comprising stopping the sample within the cell.

16. The method of claim 1, wherein measuring the optical response of the sample comprises measuring the optical response of the sample at a measurement location for a period of time, the measurement location being selected based upon the estimated concentration of the peracid or the estimated concentration of the peroxide.

17. The method of claim 1, wherein measuring the optical response of the sample comprises measuring the optical response of the sample at a measurement location for a period of time, the measurement location being selected along a mixing profile where there is an excess of the at least one reagent, the mixing profile being representative of an amount of the use composition and the at least one reagent.

18. The method of claim 17, wherein the measurement location is selected along the mixing profile where a standard deviation of the response data is at a minimum.

19. The method of claim 1, wherein the optical cell comprises a reduced-turbulence optical cell.

20. The method of claim 1, wherein determining the concentration of the peracid and the concentration of the peroxide in the use composition includes:
   determining a best fit linear relationship corresponding to the response data, wherein the best fit linear relationship includes a slope and a y-intercept; and
   selecting conversion relationships for converting the slope and the y-intercept to the concentration of the peracid and the concentration of the peroxide, wherein the selection of the conversion relationships depends upon the estimated concentration of the peracid and the estimated concentration of the peroxide.

21. The method of claim 20, wherein the conversion relationship for the concentration of the peracid is a linear relationship relative to the y-intercept, and the concentration relationship for the concentration of the peroxide is a linear relationship relative to the slope.

22. The method of claim 20, wherein the conversion relationship for the concentration of the peracid depends upon both the slope and the y-intercept, and the concentration relationship for the concentration of the peroxide depends upon both the slope and the y-intercept.

23. The method of claim 1, further comprising the step of calculating a plurality of calibration coefficients by (1) measuring an optical response of a plurality of calibration samples, each calibration sample having a known concentration of peracid and a known concentration of peroxide, and (2) optimizing a system of equations including the calibration coefficients based upon the measured optical responses of the calibration samples, wherein the calibration coefficients can then be used in the step of determining the concentrations of the peracid and the peroxide based upon the response data.

24. The method of claim 23, wherein the known concentrations of the peracid and the peroxide include the estimated concentration of the peracid and the estimated concentration of the peroxide.

25. The method of claim 1, wherein mixing the sample, delivering the sample, and measuring the optical response are performed within a temperature-regulated optical cell.

26. The method of claim 1, wherein the first wavelength and the second wavelength are between 350 nanometers and 450 nanometers.

27. The method of claim 1, wherein the first wavelength is 375 nanometers, and the second wavelength is 405 nanometers.

28. A system for determining a concentration of a peracid and a concentration of a peroxide within a use composition over a wide concentration range, the system comprising:
   an optical sensor that is configured to obtain response data from a sample that includes a volume of the use composition, and a volume of at least one reagent, wherein the response data is indicative of absorbance of the sample as a function of time at a selected wavelength; and
   a processor communicatively connected to the optical sensor, and configured to:
   select a wavelength for analyzing the sample based on at least one of an estimated concentration of the peracid or an estimated concentration of the peroxide, wherein the wavelength is selected from at least a first wavelength associated with a first estimated concentration of the peracid or a first estimated concentration of the peroxide, and a second wavelength associated with a second estimated concentration of the peracid or a second estimated concentration of the peroxide, wherein the second wavelength is greater than the first wavelength, the second estimated concentration of the peracid is greater than the first estimated concentration of the peracid, and the second estimated concentration of peroxide is greater than the first estimated concentration of peroxide; and
   determine the concentration of the peracid and the concentration of the peroxide based on the response data wherein the first estimated peracid concentration is between 100 parts per million (ppm) and 1000 ppm and the first estimated peroxide concentration is between 100 ppm and 5000 ppm, or the second estimated peracid concentration is between 1000 ppm and 5000 ppm and the second estimated peroxide concentration is between 5000 ppm and 40,000 ppm.

29. The system of claim 28, further comprising a reduced-turbulence optical cell.

30. The system of claim 28, further comprising a laminar flow mixer for mixing the sample.

31. The system of claim 30, wherein the mixer and the optical sensor are temperature regulated.

32. The system of claim 28, wherein the processor is configured to determine the concentration of the peracid as a function of a y-intercept and a slope of the response data, and the processor is configured to determine the concentration of the peroxide as a function of the slope and the y-intercept of the response data.

33. The system of claim 28, wherein the processor is configured to determine the concentration of the peracid as a function of a y-intercept of the response data, and the processor is configured to determine the concentration of the peroxide as a function of a slope of the response data.

* * * * *